(12) United States Patent
Oka et al.

(10) Patent No.: US 8,597,889 B2
(45) Date of Patent: Dec. 3, 2013

(54) METHOD FOR DETECTING CANCER CELL CAUSED BY HPV, METHOD FOR DETERMINING WHETHER OR NOT TISSUE IS AT STAGE OF HIGH-GRADE DYSPLASIA OR MORE SEVERE STAGE, AND PRIMER SET AND KIT USED THEREFOR

(75) Inventors: Noriko Oka, Kobe (JP); Masahiro Kajita, Kobe (JP)

(73) Assignee: Sysmex Corporation, Hyogo (JP)

( * ) Notice: Subject to any disclaimer, the term of this patent is extended or adjusted under 35 U.S.C. 154(b) by 138 days.

(21) Appl. No.: 12/933,841

(22) PCT Filed: Mar. 18, 2009

(86) PCT No.: PCT/JP2009/055337
§ 371 (c)(1),
(2), (4) Date: Sep. 21, 2010

(87) PCT Pub. No.: WO2009/116592
PCT Pub. Date: Sep. 24, 2009

(65) Prior Publication Data
US 2011/0020832 A1  Jan. 27, 2011

(30) Foreign Application Priority Data
Mar. 21, 2008 (JP) .................. 2008-074267

(51) Int. Cl.
*C12Q 1/68* (2006.01)
*C12P 19/34* (2006.01)

(52) U.S. Cl.
USPC ................... 435/6.12; 435/6.1; 435/6.11

(58) Field of Classification Search
None
See application file for complete search history.

(56) References Cited
U.S. PATENT DOCUMENTS
2004/0203004 A1  10/2004  Bernard et al.

FOREIGN PATENT DOCUMENTS
JP   2006-522607 A       10/2006
WO   2004090166 A1       10/2004
WO   2008/071998 A2      6/2008
WO   WO 2008071998 A2 *  6/2008

OTHER PUBLICATIONS

Badal et al., "CpG Methylation of Human Papillomavirus Type 16 DNA in Cervical Cancer Cell Lines and in Clinical Specimens: Genetic Hypomethylation Correlates with Carcinogenic Progression," Journal of Virology, 2003, vol. 77, No. 11, pp. 6227-6234.*
Wrede et al., "Absence of HPV16 and 18 DNA in breast cancer," Br. J. Cancer, 1992, vol. 65, pp. 891-894.*
Turan T. et al; "High-throughput detection of human papillomavirus-18 L1 gene methylation, a candidate biomarker for the progression of cervical neoplasia" Virology, Academic Press, Orlando, US, vol. 361, No. 1, Apr. 25, 2007, pp. 185-193, XP025884017.
Badal V et al; "CpG methylation of human papillomavirus type 16 DNA in cervical cancer cell lines and in clinical specimens: Genomic hypomethylation correlates with carcinogenic progression" Journal of Virology, The American Society of Microbiology, US, vol. 77, No. 11, Jun. 1, 2003, pp. 6227-6234, XP002330532.
Duenas-Gonzalez Alfonso et al: "Epigenetics of cervical cancer. An overview and therapeutic perspectives", Molecular Cancer, Biomed Central, London, GB, vol. 4, No. 1, Oct. 25, 2005, p. 38, XP002008261.
Tolga Turan, et al., "Methylation of the human papillomavirus-18 L1 gene: A biomarker of neoplastic progression?," Virology, 2006, pp. 175-183, vol. 349.
Mangalathu S. Rajeevan, et al., "Quantitation of site-specific HPV 16 DNA methylation by pyrosequencing," Journal of Virological Methods, 2006, pp. 170-176, vol. 138.

* cited by examiner

*Primary Examiner* — Young J Kim
(74) *Attorney, Agent, or Firm* — Sughrue Mion, PLLC

(57) ABSTRACT

Provided are a primer set, a method and a kit therefor, which can easily perform with high accuracy the detection of a cancer cell caused by HPV and the determination of whether or not a tissue is a tissue with high-grade dysplasia or in a more severe phase. As a primer set, used is a primer set consisting of a first primer which hybridizes with a nucleic acid consisting of a nucleotide sequence in which cytosine present in a site other than a CpG site is converted into another base in a nucleotide sequence having a CpG site in L1 region or L2 region of HPV and a second primer which hybridizes with a nucleic acid consisting of a nucleotide sequence in which cytosine is converted into another base in a nucleotide sequence having a CpG site in LCR or E6 region of HPV.

8 Claims, 8 Drawing Sheets

```
                        SEQUENCE LISTING

<160> NUMBER OF SEQ ID NOS: 37

<210> SEQ ID NO 1
<211> LENGTH: 35
<212> TYPE: DNA
<213> ORGANISM: Artificial
<220> FEATURE:
<223> OTHER INFORMATION: A sequence of a primer

<400> SEQUENCE: 1
ggtttataat tttttttagg aggtatatta gaaga                              35

<210> SEQ ID NO 2
<211> LENGTH: 35
<212> TYPE: DNA
<213> ORGANISM: Artificial
<220> FEATURE:
<223> OTHER INFORMATION: A sequence of a primer

<400> SEQUENCE: 2
attacataac acaataatta cacaaacatt taaaa                              35

<210> SEQ ID NO 3
<211> LENGTH: 35
<212> TYPE: DNA
<213> ORGANISM: Artificial
<220> FEATURE:
<223> OTHER INFORMATION: A sequence of a primer

<400> SEQUENCE: 3
ttaatattta ttaattgtgt tgtggttatt tattg                              35

<210> SEQ ID NO 4
<211> LENGTH: 35
<212> TYPE: DNA
<213> ORGANISM: Artificial
<220> FEATURE:
```

```
<223> OTHER INFORMATION: A sequence of a primer

<400> SEQUENCE: 4
taaccttaaa aatttaaacc ttataccaaa tatac                                  35

<210> SEQ ID NO 5
<211> LENGTH: 34
<212> TYPE: DNA
<213> ORGANISM: Artificial
<220> FEATURE:
<223> OTHER INFORMATION: A sequence of a primer

<400> SEQUENCE: 5
tattgtttat ttgtaaaatt gtatatgggt gtgt                                   34

<210> SEQ ID NO 6
<211> LENGTH: 34
<212> TYPE: DNA
<213> ORGANISM: Artificial
<220> FEATURE:
<223> OTHER INFORMATION: A sequence of a primer

<400> SEQUENCE: 6
atatctttac ttttcttcaa aacacaataa cttt                                   34

<210> SEQ ID NO 7
<211> LENGTH: 36
<212> TYPE: DNA
<213> ORGANISM: Artificial
<220> FEATURE:
<223> OTHER INFORMATION: A sequence of a primer

<400> SEQUENCE: 7
ttgttgatgt aggtgatttt tatttatatt ttagtt                                 36

<210> SEQ ID NO 8
<211> LENGTH: 29
<212> TYPE: DNA
<213> ORGANISM: Artificial
<220> FEATURE:
<223> OTHER INFORMATION: A sequence of a primer

<400> SEQUENCE: 8
ccactaatac ccacacctaa taactaacc                                         29

<210> SEQ ID NO 9
<211> LENGTH: 7904
<212> TYPE: DNA
<213> ORGANISM: Human papillomavirus type 16

<400> SEQUENCE: 9
actacaataa ttcatgtata aaactaaggg cgtaaccgaa atcggttgaa ccgaaaccgg        60
ttagtataaa agcagacatt ttatgcacca aaagagaact gcaatgtttc aggacccaca       120
ggagcgaccc agaaagttac cacagttatg cacagagctg caaacaacta tacatgatat       180
aatattagaa tgtgtgtact gcaagcaaca gttactgcga cgtgaggtat atgactttgc       240
ttttcgggat ttatgcatag tatatagaga tgggaatcca tatgctgtat gtgataaatg       300
tttaaagttt tattctaaaa ttagtgagta tagacattat tgtttatagtt tgtatggaac     360 aacattagaa cagcaataca caaaccgtt gtgtgatttg ttaattaggt gtattaactg       420
tcaaaagcca ctgtgtcctg aagaaaagca aagacatctg acaaaaagc aaagattcca       480 taatataagg ggtcggtgga ccggtcgatg tatgtcttgt tgcagatcat caagaacacg       540
```

```
tagagaaacc cagctgtaat catgcatgga gatacaccta cattgcatga atatatgtta    600
gatttgcaac cagagacaac tgatctctac tgttatgagc aattaaatga cagctcagag    660
gaggaggatg aaatagatgg tccagctgga caagcagaac cggacagagc ccattacaat    720
attgtaacct tttgttgcaa gtgtgactct acgcttcggt tgtgcgtaca agcacacac     780 gtagacattc gtactttgga agacctgtta atgggcacac taggaattgt gtgccccatc    840
tgttctcaga aaccataatc taccatggct gatcctgcag gtaccaatgg ggaagagggt    900
acgggatgta atggatggtt ttatgtagag ctgtagtgg aaaaaaaaac agggg atgct    960 atatcagatg acgagaacga aaatgacagt gatacaggtg aagatttggt agattttata    1020
gtaaatgata atgattattt aacacaggca gaaacagaga cagcacatgc gttgtttact    1080
gcacaggaag caaacaaca tagagatgca gtacaggttc taaaacgaaa gtatttggta    1140
gtccacttag tgatattagt ggatgtgtag acaataatat tagtcctaga ttaaaagcta    1200
tatgtataga aaacaaagt agagctgcaa aaggagatt atttgaaagc gaagacagcg     1260
ggtatggcaa tactgaagtg gaaactcagc agatgttaca ggtagaaggg cgccatgaga    1320
ctgaaacacc atgtagtcag tatagtggta gaagtggggg tggttgcagt cagtacagta    1380
gtggaagtgg gggagagggt gttagtgaaa gacacactat atgccaaaca ccacttacaa    1440
atattttaaa tgtactaaaa actagtaatg caaaggcagc aatgttagca aaatttaaag    1500
agttatacgg ggtgagtttt tcagaattag taagaccatt taaaagtaat aaatcaacgt    1560
gttgcgattg gtgtattgct gcatttggac ttacacccag tatagctgac agtataaaaa    1620
cactattaca acaatattgt ttatatttac acattcaaag tttagcatgt tcatggggaa    1680
tggttgtgtt actattagta agatataaat gtggaaaaaa tagagaaaca attgaaaaat    1740
tgctgtctaa actattatgt gtgtctccaa tgtgtatgat gatagagcct ccaaaattgc    1800
gtagtacagc agcagcatta tattggtata aacaggtat atcaaatatt agtgaagtgt    1860
atggagacac gccagaatgg atacaaagac aaacagtatt acaacatagt tttaatgatt    1920
gtacatttga attatcacag atggtacaat gggcctacga taatgacata gtagacgata    1980
gtgaaattgc atataaatat gcacaattgg cagacactaa tagtaatgca agtgcctttc    2040
taaaaagtaa ttcacaggca aaaattgtaa aggattgtgc aacaatgtgt agacattata    2100
aacgagcaga aaaaaaacaa atgagtatga gtcaatggat aaaatataga gtgatagggg    2160
tagatgatgg aggtgattgg aagcaaattg ttatgttttt aaggtatcaa ggtgtagagt    2220
ttatgtcatt tttaactgca ttaaaaagat ttttgcaagg catacctaaa aaaattgca    2280 tattactata tggtgcagct aacacaggta atcattatt tggtatgagt ttaatgaaat    2340
ttctgcaagg gtctgtaata tgttttgtaa attctaaaag ccattttgg ttacaaccat    2400 tagcagatgc caaaataggt atgttagatg atgctacagt gccctgttgg aactacatag    2460
atgacaattt aagaaatgca ttggatggaa atttagttc tatggatgta aagcatagac    2520
cattggtaca actaaaatgc cctccattat taattacatc taacattaat gctggtacag    2580
attctaggtg gccttattta cataatagat tggtggtgtt tacatttcct aatgagtttc    2640
catttgacga aaacggaaat ccagtgtatg agcttaatga taagaactgg aaatcctttt    2700
tctcaaggac gtggtccaga ttaagtttgc acgaggacga ggacaaggaa aacgatggag    2760
actctttgcc aacgtttaaa tgtgtgtcag acaaaatac taacacatta tgaaaatgat    2820
agtacagacc tacgtgacca tatagactat tggaaacaca tgcgcctaga atgtgctatt    2880
tattacaagg ccagagaaat gggatttaaa catattaacc accaagtggt gccaacactg    2940
```

```
gctgtatcaa agaataaagc attacaagca attgaactgc aactaacgtt agaaacaata    3000
tataactcac aatatagtaa tgaaaagtgg acattacaag acgttagcct tgaagtgtat    3060
ttaactgcac caacaggatg tataaaaaaa catggatata cagtggaagt gcagtttgat    3120
ggagacatat gcaatacaat gcattataca aactggacac atatatatat ttgtgaagaa    3180
gcatcagtaa ctgtggtaga gggtcaagtt gactattatg gtttatatta tgttcatgaa    3240
ggaatacgaa catattttgt gcagtttaaa gatgatgcag aaaaatatag taaaaataaa    3300
gtatgggaag ttcatgcggg tggtcaggta atattatgtc ctacatctgt gtttagcagc    3360
aacgaagtat cctctcctga aattattagg cagcacttgg ccaaccaccc cgccgcgacc    3420
cataccaaag ccgtcgcctt gggcaccgaa gaaacacaga cgactatcca gcgaccaaga    3480
tcagagccag acaccggaaa cccctgccac accactaagt tgttgcacag agactcagtg    3540
gacagtgctc caatcctcac tgcatttaac agctcacaca aaggacggat taactgtaat    3600
agtaacacta cacccatagt acatttaaaa ggtgatgcta atactttaaa atgtttaaga    3660
tatagattta aaaagcattg tacattgtat actgcagtgt cgtctacatg gcattggaca    3720
ggacataatg taaaacataa aagtgcaatt gttacactta catatgatag tgaatggcaa    3780
cgtgaccaat ttttgtctca agttaaaata ccaaaaacta ttacagtgtc tactggattt    3840
atgtctatat gacaaatctt gatactgcat ccacaacatt actggcgtgc ttttttgcttt   3900 gctttgtgtg cttttgtgtg tctgcctatt aatacgtccg ctgcttttgt ctgtgtctac    3960
atacacatca ttaataatat tggtattact attgtggata acagcagcct ctgcgtttag    4020
gtgttttatt gtatatatta tatttgttta tataccatta ttttaatac atacacatgc      4080 acgcttttta attacataat gtatatgtac ataatgtaat tgttacatat aattgttgta    4140
taccataact tactattttt tcttttttat tttcatatat aattttttt tttgtttgtt      4200 tgtttgtttt ttaataaact gttattactt aacaatgcga cacaaacgtt ctgcaaaacg    4260
cacaaaacgt gcatcggcta cccaacttta taaaacatgc aaacaggcag gtacatgtcc    4320
acctgacatt atacctaagg ttgaaggcaa aactattgct gaacaaatat tacaatatgg    4380
aagtatgggt gtattttttg gtgggttagg aattggaaca gggtcgggta caggcggacg    4440
cactgggtat attccattgg gaacaaggcc tcccacagct acagatacac ttgctcctgt    4500
aagaccccct ttaacagtag atcctgtggg cccttctgat ccttctatag tttctttagt    4560
ggaagaaact agttttattg atgctggtgc accaacatct gtaccttcca ttcccccaga    4620
tgtatcagga tttagtatta ctacttcaac tgataccaca cctgctatat tagatattaa    4680
taatactgtt actactgtta ctacacataa taatcccact ttcactgacc catctgtatt    4740
gcagcctcca cacctgcag aaactggagg gcattttaca cttcatcat ccactattag      4800 tacacataat tatgaagaaa ttcctatgga tacatttatt gttagcacaa accctaacac    4860
agtaactagt agcacaccca taccagggtc tcgcccagtg gcacgcctag gattatatag    4920
tcgcacaaca caacaggtta aagttgtaga ccctgctttt gtaaccactc ccactaaact    4980
tattacatat gataatcctg catatgaagg tatagatgtg gataatacat tatattttc     5040 tagtaatgat aatagtatta atatagctcc agatcctgac ttttggata tagttgcttt     5100 acataggcca gcattaacct ctaggcgtac tggcattagg tacagtagaa ttggtaataa    5160
acaaacacta cgtactcgta gtggaaaatc tataggtgct aaggtacatt attattatga    5220
tttaagtact attgatcctg cagaagaaat agaattacaa actataacac cttctacata    5280
tactaccact tcacatgcag cctcacctac ttctattaat aatggattat atgatattta    5340
```

```
tgcagatgac tttattacag atacttctac aacccggta  ccatctgtac cctctacatc  5400
tttatcaggt tatattcctg caaatacaac aattccttt  ggtggtgcat acaatattcc  5460
tttagtatca ggtcctgata tacccattaa tataactgac caagctcctt cattaattcc  5520
tatagttcca gggtctccac aatatacaat tattgctgat gcaggtgact tttatttaca  5580
tcctagttat tacatgttac gaaaacgacg taaacgttta ccatatttt  tttcagatgt  5640 ctctttggct gcctagtgag gccactgtct acttgcctcc tgtcccagta tctaaggttg  5700
taagcacgga tgaatatgtt gcacgcacaa acatatatta tcatgcagga acatccagac  5760
tacttgcagt tggacatccc tattttccta ttaaaaaacc taacaataac aaaatattag  5820
ttcctaaagt atcaggatta caatacaggg tatttagaat acatttacct gaccccaata  5880
agtttggttt tcctgacacc tcattttata atccagatac acagcggctg gtttgggcct  5940
gtgtaggtgt tgaggtaggt cgtggtcagc cattaggtgt gggcattagt ggccatcctt  6000
tattaaataa attggatgac acagaaaatg ctagtgctta tgcagcaaat gcaggtgtgg  6060
ataatagaga atgtatatct atggattaca aacaaacaca attgtgttta attggttgca  6120
aaccacctat aggggaacac tggggcaaag gatccccatg taccaatgtt gcagtaaatc  6180
caggtgattg tccaccatta gagttaataa acacagttat tcaggatggt gatatggttc  6240
atactggctt tggtgctatg gactttacta cattacaggc taacaaaagt gaagttccac  6300
tggatatttg tacatctatt tgcaaatatc cagattatat taaaatggtg tcagaaccat  6360
atggcgacag cttattttt  tatttacgaa gggaacaaat gtttgttaga catttattta  6420
atagggctgg tactgttggt gaaaatgtac cagacgattt atacattaaa ggctctgggt  6480
ctactgcaaa tttagccagt tcaaattatt ttcctacacc tagtggttct atggttacct  6540
ctgatgccca aatattcaat aaaccttatt ggttacaacg agcacagggc cacaataatg  6600
gcatttgttg gggtaaccaa ctatttgtta ctgttgttga tactacacgc agtacaaata  6660
tgtcattatg tgctgccata tctacttcag aaactacata taaaaatact aactttaagg  6720
agtacctacg acatggggag gaatatgatt tacagtttat ttttcaactg tgcaaaataa  6780
ccttaactgc agacgttatg acatacatac attctatgaa ttccactatt ttggaggact  6840
ggaattttgg tctacaacct ccccaggag  gcacactaga agatacttat aggtttgtaa  6900
cccaggcaat tgcttgtcaa aaacatacac ctccagcacc taaagaagat gatcccctta  6960
aaaaatacac ttttggggaa gtaaatttaa aggaaaagtt ttctgcagac ctagatcagt  7020 ttccttagg  acgcaaattt ttactacaag caggattgaa ggccaaacca aaatttacat  7080
taggaaaacg aaaagctaca cccaccacct catctacctc tacaactgct aaacgcaaaa  7140
aacgtaagct gtaagtattg tatgtatgtt gaattagtgt tgtttgttgt gtatatgttt  7200
gtatgtgctt gtatgtgctt gtaaatatta agttgtatgt gtgtttgtat gtatggtata  7260
ataaacacgt gtgtatgtgt ttttaaatgc ttgtgtaact attgtgtcat gcaacataaa  7320
taaacttatt gtttcaacac ctactaattg tgttgtggtt attcattgta tataaactat  7380
atttgctaca tcctgttttt gttttatata tactatattt tgtagcgcca ggcccatttt  7440
gtagcttcaa ccgaattcgg ttgcatgctt tttggcacaa aatgtgtttt tttaaatagt  7500
tctatgtcag caactatggt ttaaacttgt acgtttcctg cttgccatgc gtgccaaatc  7560
cctgttttcc tgacctgcac tgcttgccaa ccattccatt gttttttaca ctgcactatg  7620
tgcaactact gaatcactat gtacattgtg tcatataaaa taaatcacta tgcgccaacg  7680
ccttacatac cgctgttagg cacatatttt tggcttgttt taactaacct aattgcatat  7740
```

```
ttggcataag gtttaaactt ctaaggccaa ctaaatgtca ccctagttca tacatgaact    7800
gtgtaaaggt tagtcataca ttgttcattt gtaaaactgc acatgggtgt gtgcaaaccg    7860
attttgggtt acacatttac aagcaactta tataataata ctaa                    7904
```

```
<210> SEQ ID NO 10
<211> LENGTH: 34
<212> TYPE: DNA
<213> ORGANISM: Artificial
<220> FEATURE:
<223> OTHER INFORMATION: A sequence of a primer

<400> SEQUENCE: 10
gaaggttaaa ttaaaattta tattaggaaa acga                               34

<210> SEQ ID NO 11
<211> LENGTH: 35
<212> TYPE: DNA
<213> ORGANISM: Artificial
<220> FEATURE:
<223> OTHER INFORMATION: A sequence of a primer

<400> SEQUENCE: 11
aattcaatta aaactacaaa ataaccacta acact                              35

<210> SEQ ID NO 12
<211> LENGTH: 30
<212> TYPE: DNA
<213> ORGANISM: Artificial
<220> FEATURE:
<223> OTHER INFORMATION: A sequence of a primer

<400> SEQUENCE: 12
gttggtattg ttggtgaaaa tgtattagac                                    30

<210> SEQ ID NO 13
<211> LENGTH: 33
<212> TYPE: DNA
<213> ORGANISM: Artificial
<220> FEATURE:
<223> OTHER INFORMATION: A sequence of a primer

<400> SEQUENCE: 13
ccaacaaata ccattattat aaccctatac tcg                                33

<210> SEQ ID NO 14
<211> LENGTH: 24
<212> TYPE: DNA
<213> ORGANISM: Artificial
<220> FEATURE:
<223> OTHER INFORMATION: A sequence of a primer

<400> SEQUENCE: 14
tgtatgtttt tgtttgtta tgtg                                           24

<210> SEQ ID NO 15
<211> LENGTH: 30
<212> TYPE: DNA
<213> ORGANISM: Artificial
<220> FEATURE:
<223> OTHER INFORMATION: A sequence of a primer

<400> SEQUENCE: 15
tacctaacaa caatatataa aacattaaca                                    30

<210> SEQ ID NO 16
```

-continued

```
<211> LENGTH: 7857
<212> TYPE: DNA
<213> ORGANISM: Human papillomavirus type 18

<400> SEQUENCE: 16
attaatactt ttaacaattg tagtatataa aaaagggagt aaccgaaaac ggtcgggacc      60
gaaaacggtg tatataaaag atgtgagaaa cacaccacaa tactatggcg cgctttgagg     120
atccaacacg gcgaccctac aagctacctg atctgtgcac ggaactgaac acttcactgc     180
aagacataga ataacctgtg tatattgcaa agacagtatt ggaacttaca gaggtatttg     240
aatttgcatt taaagattta tttgtggtgt atagagacag tataccccat gctgcatgcc     300
ataaatgtat agatttttat tctagaatta gagaattaag acattattca gactctgtgt     360
atggagacac attggaaaaa ctaactaaca ctgggttata caatttatta ataaggtgcc     420
tgcggtgcca gaaaccgttg aatccagcag aaaaacttag acaccttaat gaaaaacgac     480
gatttcacaa catagctggg cactatagag gccagtgcca ttcgtgctgc aaccgagcac     540
gacaggaacg actccaacga cgcagagaaa cacaagtata atattaagta tgcatggacc     600
taaggcaaca ttgcaagaca ttgtattgca tttagagccc caaaatgaaa ttccggttga     660
ccttctatgt cacgagcaat taagcgactc agaggaagaa aacgatgaaa tagatggagt     720
taatcatcaa catttaccag cccgacgagc cgaaccacaa cgtcacacaa tgttgtgtat     780
gtgttgtaag tgtgaagcca gaattgagct agtagtagaa agctcagcag acgaccttcg     840
agcattccag cagctgtttc tgaacaccct gtcctttgtg tgtccgtggt gtgcatccca     900
gcagtaagca acaatggctg atccagaagg tacagacggg gagggcacgg ttgtaacgg      960 ctggttttat gtacaagcta ttgtagacaa aaaaacagga gatgtaatat cagatgacga    1020
ggacgaaaat gcaacagaca cagggtcgga tatggtagat tttattgata cacaaggaac    1080
attttgtgaa caggcagagc tagagacagc acaggcattg ttccatgcgc aggaggtcca    1140
caatgatgca caagtgttgc atgttttaaa acgaaagttt gcaggaggca gcacagaaaa    1200
cagtccatta ggggagcggc tggaggtgga tacagagtta agtccacggt tacaagaaat    1260
atctttaaat agtgggcaga aaaggcaaa aaggcggctg tttacaatat cagatagtgg    1320
ctatggctgt tctgaagtgg aagcaacaca gattcaggta actacaaatg cgaacatgg     1380 cggcaatgta tgtagtggcg gcagtacgga ggctatagac aacggggggca cagagggcaa    1440 caacagcagt gtagacggta caagtgacaa tagcaatata gaaaatgtaa atccacaatg    1500
taccatagca caattaaaag acttgttaaa agtaaacaat aaacaaggag ctatgttagc    1560
agtatttaaa gacacatatg gctatcatt tacagattta gttagaaatt ttaaaagtga    1620
taaaaccacg tgtacagatt gggttacagc tatatttgga gtaaacccaa caatagcaga    1680
aggatttaaa acactaatac agccatttat attatatgcc catattcaat gtctagactg    1740
taaatgggga gtattaatat tagccctgtt gcgttacaaa tgtggtaaga gtagactaac    1800
agttgctaaa ggtttaagta cgttgttaca cgtacctgaa acttgtatgt taattcaacc    1860
accaaaattg cgaagtagtg ttgcagcact atattggtat agaacaggaa tatcaaatat    1920
tagtgaagta atgggagaca caccctgagtg gatacaaaga cttactatta taacacatgg    1980
aatagatgat agcaattttg atttgtcaga aatggtacaa tggcatttg ataatgagct     2040 gacagatgaa agcgatatgg catttgaata tgccttatta gcagacagca acagcaatgc    2100
agctgccttt ttaaaaagca attgccaagc taaatattta aaagattgtg ccacaatgtg    2160
caaacattat aggcgagccc aaaaacgaca aatgaatatg tcacagtgga tacgatttag    2220
```

```
atgttcaaaa atagatgaag ggggagattg gagaccaata gtgcaattcc tgcgatacca   2280
acaaatagag tttataacat ttttaggagc cttaaaatca tttttaaaag gaaccccaa    2340
aaaaaattgt ttagtatttt gtggaccagc aaatacagga aaatcatatt ttggaatgag   2400
ttttatacac tttatacaag gagcagtaat atcatttgtg aattccacta gtcattttg    2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat ttgaatttcc   2700
aaatgcattt ccatttgata aaaatggcaa tccagtatat gaaataaatg acaaaaattg   2760
gaaatgtttt tttgaaagga catggtccag attagatttg cacgaggaag aggaagatgc   2820
agacaccgaa ggaaacccctt tcggaacgtt taagttgcgt gcaggacaaa atcatagacc   2880
actatgaaaa tgacagtaaa gacatagaca gccaaataca gtattggcaa ctaatacgtt   2940
gggaaaatgc aatattcttt gcagcaaggg aacatggcat acagacatta aaccaccagg   3000
tggtgccagc ctataacatt tcaaaaagta aagcacataa agctattgaa ctgcaaatgg   3060
ccctacaagg ccttgcacaa agtcgataca aaaccgagga ttggacactg caagacacat   3120
gcgaggaact atggaataca gaacctactc actgctttaa aaaaggtggc caaacagtac   3180
aagtatattt tgatggcaac aaagacaatt gtatgaccta tgtagcatgg gacagtgtgt   3240
attatatgac tgatgcagga acatgggaca aaaccgctac ctgtgtaagt cacaggggat   3300
tgtattatgt aaaggaaggg tacaacacgt tttatataga atttaaaagt gaatgtgaaa   3360
aatatgggaa cacaggtacg tgggaagtac attttgggaa taatgtaatt gattgtaatg   3420
actctatgtg cagtaccagt gacgacacgg tatccgctac tcagcttgtt aaacagctac   3480
agcacacccc ctcaccgtat tccagcaccg tgtccgtggg caccgcaaag acctacggcc   3540
agacgtcggc tgctacacga cctggacact gtggactcgc ggagaagcag cattgtggac   3600
ctgtcaaccc acttctcggt gcagctacac ctacaggcaa caacaaaaga cggaaactct   3660
gtagtggtaa cactacgcct ataatacatt taaaaggtga cagaaacagt ttaaaatgtt   3720
tacggtacag attgcgaaaa catagcgacc actatagaga tatatcatcc acctggcatt   3780
ggacaggtgc aggcaatgaa aaaacaggaa tactgactgt aacataccat agtgaaacac   3840
aaagaacaaa attttttaaat actgttgcaa ttccagatag tgtacaaata ttggtgggat   3900
acatgacaat gtaatacata tgctgtagta ccaatatgtt atcacttatt tttttatttt   3960
gcttttgtgt atgcatgtat gtgtgctgcc atgtcccgct tttgccatct gtctgtatgt   4020
gtgcgtatgc atgggtattg gtatttgtgt atattgtggt aataacgtcc cctgccacag   4080
cattcacagt atatgtattt tgttttttat tgcccatgtt actattgcat atacatgcta   4140
tattgtcttt acagtaattg tataggttgt tttatacagt gtattgtaca ttgtatattt   4200
tgttttatac cttttatgct ttttgtattt ttgtaataaa agtatggtat cccaccgtgc   4260
cgcacgacgc aaacgggctt cggtaactga cttatataaa acatgtaaac aatctggtac   4320
atgtccacct gatgttgttc ctaaggtgga gggcaccacg ttagcagata aaatattgca   4380
atggtcaagc cttggtatat ttttgggtgg acttggcata ggtactggca gtggtacagg   4440
gggtcgtaca gggtacattc cattgggtgg gcgttccaat acagtggtgg atgttggtcc   4500
tacacgtccc ccagtggtta ttgaacctgt gggccccaca gacccatcta ttgttacatt   4560
aatagaggac tccagtgtgg ttacatcagg tgcacctagg cctacgttta ctggcacgtc   4620
```

```
tgggtttgat ataacatctg cgggtacaac tacacctgcg gttttggata tcacaccttc    4680
gtctacctct gtgtctattt ccacaaccaa ttttaccaat cctgcatttt ctgatccgtc    4740
cattattgaa gttccacaaa ctggggaggt ggcaggtaat gtatttgttg gtaccectac    4800 atctggaaca catgggtatg aggaaatacc tttacaaaca tttgcttctt ctggtacggg    4860
ggaggaaccc attagtagta ccccattgcc tactgtgcgg cgtgtagcag gtccccgcct    4920
ttacagtagg gcctaccaac aagtgtcagt ggctaaccct gagtttctta cacgtccatc    4980
ctctttaatt acatatgaca acccggcctt tgagcctgtg gacactacat taacatttga    5040
tcctcgtagt gatgttcctg attcagattt tatggatatt atccgtctac ataggcctgc    5100
tttaacatcc aggcgtggga ctgttcgctt tagtagatta ggtcaacggg caactatgtt    5160
tacccgcagc ggtacacaaa taggtgctag ggttcacttt tatcatgata taagtcctat    5220
tgcaccttcc ccagaatata ttgaactgca gcctttagta tctgccacgg aggacaatga    5280
cttgtttgat atatatgcag atgacatgga ccctgcagtg cctgtaccat cgcgttctac    5340
tacctccttt gcatttttta aatattcgcc cactatatct tctgcctctt cctatagtaa    5400
tgtaacggtc cctttaacct cctcttggga gtgtcctgta tacacgggtc ctgatattac    5460
attaccatct actacctctg tatggcccat tgtatcaccc acggccctg cctctacaca    5520 gtatattggt atacatggta cacattatta tttgtggcca ttatattatt ttattcctaa    5580
gaaacgtaaa cgtgttccct atttttttgc agatggcttt gtggcggcct agtgacaata    5640
ccgtatatct tccacctcct tctgtggcaa gagttgtaaa taccgatgat tatgtgactc    5700
ccacaagcat attttatcat gctggcagct ctagattatt aactgttggt aatccatatt    5760
ttagggttcc tgcaggtggt ggcaataagc aggatattcc taaggtttct gcataccaat    5820
atagagtatt tagggtgcag ttacctgacc caaataaatt tggtttacct gatactagta    5880
tttataatcc tgaaacacaa cgtttagtgt gggcctgtgc tggagtggaa attggccgtg    5940
gtcagccttt aggtgttggc cttagtgggc atccatttta taataaatta gatgacactg    6000
aaagttccca tgccgccacg tctaatgttt ctgaggacgt tagggacaat gtgtctgtag    6060
attataagca gacacagtta tgtattttgg gctgtgcccc tgctattggg gaacactggg    6120
ctaaaggcac tgcttgtaaa tcgcgtcctt tatcacaggg cgattgcccc cctttagaac    6180
ttaaaaacac agttttggaa gatggtgata tggtagatac tggatatggt gccatggact    6240
ttagtacatt gcaagatact aaatgtgagg taccattgga tatttgtcag tctatttgta    6300
aatatcctga ttatttacaa atgtctgcag atccttatgg ggattccatg ttttttttgc    6360
tacggcgtga gcagcttttt gctaggcatt tttggaatag agcaggtact atgggtgaca    6420
ctgtgcctca atccttatat attaaaggca caggtatgcc tgcttcacct ggcagctgtg    6480
tgtattctcc ctctccaagt ggctctattg ttacctctga ctcccagttg tttaataaac    6540
catattggtt acataaggca cagggtcata acaatggtgt tgctggcat aatcaattat    6600 ttgttactgt ggtagatacc actcccagta ccaatttaac aatatgtgct tctacacagt    6660
ctcctgtacc tggcaatat gatgctacca aatttaagca gtatagcaga catgttgagg    6720
aatatgattt gcagtttatt tttcagttgt gtactattac tttaactgca gatgttatgt    6780
cctatattca tagtatgaat agcagtattt tagaggattg gaactttggt gttcccccc    6840 ccccaactac tagtttggtg gatacatatc gttttgtaca atctgttgct attacctgtc    6900
aaaaggatgc tgcaccggct gaaaataagg atccctatga taagttaaag ttttggaatg    6960
tggatttaaa ggaaaagttt tctttagact tagatcaata tccccttgga cgtaaatttt    7020
```

-continued

```
tggttcaggc tggattgcgt cgcaagccca ccataggccc tcgcaaacgt tctgctccat    7080
ctgccactac gtcttctaaa cctgccaagc gtgtgcgtgt acgtgccagg aagtaatatg    7140
tgtgtgtgta tatatatata catctattgt tgtgtttgta tgtcctgtgt ttgtgtttgt    7200
tgtatgattg cattgtatgg tatgtatggt tgttgttgta tgttgtatgt tactatattt    7260
gttggtatgt ggcattaaat aaaatatgtt ttgtggttct gtgtgttatg tggttgcgcc    7320
ctagtgagta acaactgtat ttgtgtttgt ggtatgggtg ttgcttgttg ggctatatat    7380
tgtcctgtat ttcaagttat aaaactgcac accttacagc atccatttta tcctacaatc    7440
ctccattttg ctgtgcaacc gatttcggtt gcctttggct tatgtctgtg gttttctgca    7500
caatacagta cgctggcact attgcaaact ttaatctttt gggcactgct cctacatatt    7560
ttgaacaatt ggcgcgcctc tttgcgcat ataaggcgca cctggtatta gtcatttcc     7620 tgtccaggtg cgctacaaca attgcttgca taactatatc cactccctaa gtaataaaac    7680 tgctttagg cacatatttt agtttgtttt tacttaagct aattgcatac ttggcttgta     7740
caactacttt catgtccaac attctgtcta cccttaacat gaactataat atgactaagc    7800
tgtgcataca tagtttatgc aaccgaaata ggttgggcag cacatactat actttc       7857
```

<210> SEQ ID NO 17
<211> LENGTH: 24
<212> TYPE: DNA
<213> ORGANISM: Artificial
<220> FEATURE:
<223> OTHER INFORMATION: A sequence of a primer

<400> SEQUENCE: 17
taaaatatgt tttgtggttt tgtg                                              24

<210> SEQ ID NO 18
<211> LENGTH: 27
<212> TYPE: DNA
<213> ORGANISM: Artificial
<220> FEATURE:
<223> OTHER INFORMATION: A sequence of a primer

<400> SEQUENCE: 18
ataattatac aaaccaaata tacaatt                                           27

<210> SEQ ID NO 19
<211> LENGTH: 25
<212> TYPE: DNA
<213> ORGANISM: Artificial
<220> FEATURE:
<223> OTHER INFORMATION: A sequence of a primer

<400> SEQUENCE: 19
agatttagat taatattttt ttgga                                             25

<210> SEQ ID NO 20
<211> LENGTH: 26
<212> TYPE: DNA
<213> ORGANISM: Artificial
<220> FEATURE:
<223> OTHER INFORMATION: A sequence of a primer

<400> SEQUENCE: 20
aaattaaaat ttacaataat accaac                                            26

<210> SEQ ID NO 21
<211> LENGTH: 33
<212> TYPE: DNA

```
<213> ORGANISM: Artificial
<220> FEATURE:
<223> OTHER INFORMATION: A sequence of a primer

<400> SEQUENCE: 21
gttatttgat ttaaataaat ttggtttatt tga                                    33

<210> SEQ ID NO 22
<211> LENGTH: 28
<212> TYPE: DNA
<213> ORGANISM: Artificial
<220> FEATURE:
<223> OTHER INFORMATION: A sequence of a primer

<400> SEQUENCE: 22
ccaaaaatac ctaacaaaaa actactca                                          28

<210> SEQ ID NO 23
<211> LENGTH: 29
<212> TYPE: DNA
<213> ORGANISM: Artificial
<220> FEATURE:
<223> OTHER INFORMATION: A sequence of a primer

<400> SEQUENCE: 23
tgtttaatat tttgtttatt tttaatatg                                         29

<210> SEQ ID NO 24
<211> LENGTH: 26
<212> TYPE: DNA
<213> ORGANISM: Artificial
<220> FEATURE:
<223> OTHER INFORMATION: A sequence of a primer

<400> SEQUENCE: 24
tatcttacaa taaaatattc aattcc                                            26

<210> SEQ ID NO 25
<211> LENGTH: 23
<212> TYPE: DNA
<213> ORGANISM: Artificial
<220> FEATURE:
<223> OTHER INFORMATION: A sequence of a primer

<400> SEQUENCE: 25
atatataacc caacaaacaa cac                                               23

<210> SEQ ID NO 26
<211> LENGTH: 27
<212> TYPE: DNA
<213> ORGANISM: Artificial
<220> FEATURE:
<223> OTHER INFORMATION: A sequence of a primer

<400> SEQUENCE: 26
tccataacac catatccaat atctacc                                           27

<210> SEQ ID NO 27
<211> LENGTH: 21
<212> TYPE: DNA
<213> ORGANISM: Artificial
<220> FEATURE:
<223> OTHER INFORMATION: A sequence of a primer

<400> SEQUENCE: 27
tggttagtga attttatggg g                                                 21
```

```
<210> SEQ ID NO 28
<211> LENGTH: 30
<212> TYPE: DNA
<213> ORGANISM: Artificial
<220> FEATURE:
<223> OTHER INFORMATION: A sequence of a primer

<400> SEQUENCE: 28
ttacaaaact aaaaaacaaa ctataaatca                              30

<210> SEQ ID NO 29
<211> LENGTH: 24
<212> TYPE: DNA
<213> ORGANISM: Artificial
<220> FEATURE:
<223> OTHER INFORMATION: A sequence of a primer

<400> SEQUENCE: 29
atggtgttga ttttatgttg tatt                                    24

<210> SEQ ID NO 30
<211> LENGTH: 25
<212> TYPE: DNA
<213> ORGANISM: Artificial
<220> FEATURE:
<223> OTHER INFORMATION: A sequence of a primer

<400> SEQUENCE: 30
aactatcccc tacctatttc aaaac                                   25

<210> SEQ ID NO 31
<211> LENGTH: 24
<212> TYPE: DNA
<213> ORGANISM: Artificial
<220> FEATURE:
<223> OTHER INFORMATION: A sequence of a primer

<400> SEQUENCE: 31
ttaatatttt ggaggattgg taat                                    24

<210> SEQ ID NO 32
<211> LENGTH: 30
<212> TYPE: DNA
<213> ORGANISM: Artificial
<220> FEATURE:
<223> OTHER INFORMATION: A sequence of a primer

<400> SEQUENCE: 32
atataataaa ataatataaa taccacaaca                              30

<210> SEQ ID NO 33
<211> LENGTH: 29
<212> TYPE: DNA
<213> ORGANISM: Artificial
<220> FEATURE:
<223> OTHER INFORMATION: A sequence of a primer

<400> SEQUENCE: 33
aattaggttt taaagtaaag tttagatta                               29

<210> SEQ ID NO 34
<211> LENGTH: 29
<212> TYPE: DNA
<213> ORGANISM: Artificial
<220> FEATURE:
<223> OTHER INFORMATION: A sequence of a primer
```

-continued

<400> SEQUENCE: 34
ttatttaaat tataatttaa aaaaaacac                                29

<210> SEQ ID NO 35
<211> LENGTH: 26
<212> TYPE: DNA
<213> ORGANISM: Artificial
<220> FEATURE:
<223> OTHER INFORMATION: A sequence of a primer

<400> SEQUENCE: 35
ttttattttt attttgtgta tgtaat                                   26

<210> SEQ ID NO 36
<211> LENGTH: 25
<212> TYPE: DNA
<213> ORGANISM: Artificial
<220> FEATURE:
<223> OTHER INFORMATION: A sequence of a primer

<400> SEQUENCE: 36
taatcctaca ataacctacc aaaaa                                    25

<210> SEQ ID NO 37
<211> LENGTH: 7824
<212> TYPE: DNA
<213> ORGANISM: Human papillomavirus type 58

<400> SEQUENCE: 37
ctaaactata atgccaaatc ttgtaaaaac tagggtgtaa ccgaaaacgg tctgaccgaa      60
accggtgcat atataaagca gacatttttt ggtaggctac tgcaggacta tgttccagga    120
cgcagaggag aaaccacgga cattgcatga tttgtgtcag gcgttggaga catctgtgca    180
tgaaatcgaa ttgaaatgcg ttgaatgcaa aaagactttg cagcgatctg aggtatatga    240 cttttgtattt gcagatttaa gaatagtgta tagagatgga aatccatttg cagtatgtaa    300
agtgtgctta cgattgctat ctaaaataag tgagtataga cattataatt attcgctata    360
tggagacaca ttagaacaaa cactaaaaaa gtgtttaaat gaaatattaa ttagatgtat    420
tatttgtcaa agaccattgt gtccacaaga aaaaaaaagg catgtggatt taaacaaaag    480
gtttcataat atttcgggtc gttggacagg gcgctgtgca gtgtgttgga gaccccgacg    540
tagacaaaca caagtgtaac ctgtaacaac gccatgagag gaaacaaccc aacgctaaga    600
gaatatattt tagatttaca tcctgaacca actgacctat tctgctatga gcaattatgt    660
gacagctcag acgaggatga aataggcttg gacgggccag atggacaagc acaaccggcc    720
acagctaatt actacattgt aacttgttgt tacacttgtg gcaccacggt tcgtttgtgt    780
atcaacagta caacaaccga cgtacgaacc ctacagcagc tgcttatggg cacatgtacc    840
attgtgtgcc ctagctgtgc acagcaataa acaccatctg caatgatgga ccctgaaggt    900
acaaacgggg taggggcggg ctgtactggc tggtttgagg tagaagcggt aatagaacga    960
agaacaggag ataatatttc agatgatgag gacgaaacag cagacgatag tggtacagat   1020
ttaatagagt ttatagatga ttcagtacaa agtactacac aggcagaagc agaggcagcc   1080
cgagcgttgt ttaatgtaca ggaaggggtg gacgatataa atgctgtgtg tgcactaaaa   1140
cgaaagtttg cagcatgctc agaaagtgct gtagaggact gtgtggaccg ggctgcaaat   1200
gtgtgtgtat cgtggaaata taaaaataaa gaatgcacac acagaaacg aaaaattatt   1260 gagctagaag acagcggata tggcaatact gaagtggaaa ctgagcagat ggcacaccag   1320

```
gtagaaagcc aaaatggcga cgcagactta aatgactcgg agtctagtgg ggtgggggct    1380
agttcagatg taagcagtga aacgatgta dacagttgta atactgttcc attacaaaat    1440
attagtaata ttctacataa cagtaatact aaagcaacgc tattatataa attcaaagaa    1500
gcttatggag taagttttat ggaattagtt agaccattta aaagtgataa aacaagctgt    1560
acagattggt gtataacagg gtatggaata agtccctccg tagcagaaag tttaaaagta    1620
ctaattaaac agcacagtat atatacacac ctacaatgtt taacgtgtga cagaggaatt    1680
atattattat tgttaattag atttaaatgt agcaaaaata gattaactgt ggcaaaatta    1740
atgagtaatt tactatcaat tcctgaaaca tgtatgatta tcgagccacc aaaattacga    1800
agtcaagcat gtgccttata ttggtttaga acagcaatgt caaatataag tgatgtgcaa    1860
gggacaacac cagaatggat agatagatta acagtgttac agcatagctt taatgatgat    1920
atatttgatt taagtgaaat gatacaatgg gcatatgata atgacattac agatgatagt    1980
gacattgcat ataaatatgc acagttagca gatgttaata gtaatgcagc agcattttta    2040
agaagcaatg cacaagcaaa aatagtaaaa gactgtggcg ttatgtgcag acattataaa    2100
agagcagaaa agcgtggtat gacaatggga caatggatac aaagtaggtg tgaaaaaaca    2160
aatgatggag gtaattggag accaatagta caattttaa gatatcaaaa tattgaattt    2220
acagcatttt tagttgcatt taaacagttt ttacaaggtg taccaaaaaa aagttgtatg    2280
ttactgtgtg gcccagcaaa tacagggaaa tcatattttg gaatgagttt aatacatttt    2340
ttaaaaggat gcattatttc atatgtaaat tccaaaagtc atttttggtt gcagccatta    2400
tcagatgcta aactaggtat gatagatgat gtaacagcca taagctggac atatatagat    2460
gattatatga gaaatgcatt agatggtaac gacatttcaa tagatgtaaa acatagggca    2520
ttagtacaat taaaatgtcc accattaata attacctcaa atacaaatgc aggcaaagat    2580
tcacgatggc catatttgca cagtagacta acagtatttg aatttaacaa tccatttcca    2640
tttgatgcaa atggtaatcc agtgtataaa ataaatgatg aaaattggaa atccttttttc    2700 tcaaggacgt ggtgcaaatt aggcttaata gaggaagagg acaaggaaaa cgatggagga    2760
aatatcagca cgtttaagtg cagtgcagga caaaatccta gacatatacg aagctgataa    2820
aaatgattta acatcacaaa ttgaacattg gaaactaata cgcatggagt gtgctataat    2880
gtatacagcc agacaaatgg gaatatcaca tttgtgccac caggtggtgc cgtcattggt    2940
agcatcaaag actaaagcgt ttcaagtaat tgaactgcaa atggcattag agacattaaa    3000
tgcatcacca tataaaacag atgaatggac attgcaacaa acaagcttag aagtgtggtt    3060
atcagagcca caaaaatgct ttaaaaaaaa aggcataaca gtaactgtac aatatgacaa    3120
tgataaagca aacacaatgg attatacaaa ttggagtgaa atatatatta ttgaggaaac    3180
aacatgtact ttggtagcag gagaagttga ctatgtgggg ttgtattata tacatggcaa    3240
tgaaaagacg tattttaaat attttaaaga ggatgcaaaa aagtactcta aaacacaatt    3300
atgggaggta catgtgggta gtcgggtaat tgtatgtcct acatctatac ctagtgatca    3360
aatatccact actgaaactg ctgacccaaa gaccaccgag gccaccaaca acgaaagtac    3420 acagggggaca aagcgacgac gactcgattt accagactcc agagacaaca cccagtactc    3480
cacaaagtat acagactgcg ccgtggacag tagaccacga ggaggaggac tacacagtac    3540
aactaactgt acatacaaag ggcggaacgt gtgtagttct aaagtttcac ctatcgtgca    3600
tttaaaaggt gacccaaata gtttaaaatg tttaagatat agattaaaac catttaaaga    3660
cttatactgt aatatgtcat ccacatggca ttggaccagt gatgacaaag gtgacaaagt    3720
```

-continued

```
aggaattgtt actgtaacat acacaacgga aacacaacga caactgtttt taaacactgt    3780
taaaatacca cccactgtgc aaataagtac tggtgttatg tcattgtaat tgtattgtac    3840
aattactgta tgtaaaccac aagccaatat gtgctgctaa gtgtatatac aatgatatta    3900
cctatttttg ttgtttgttt tatactgttt ttatgcttgt gcattttttt gcggccattg    3960
gtgctatcta tttctatata tgcttggttg ctggtgttgg tgttgctgct ttgggtgtct    4020
gtggggtcgg ctctacgaat ttttttctgt tacttaatat ttttatatat accaatgatg    4080
tgtattaatt ttcatgcaca atacttaacc caacaagact aactgtatac tggttctgca    4140
catggtggta tggtattgta aatatttact gttgtgtgtg ttgttttttat tattttttata    4200
catttactaa taaatacttt tatattttta gcactgtctt attatgagac acaaacggtc    4260
tacaaggcgc aagcgtgcat ctgctacaca actttaccaa acatgcaagg cctcaggcac    4320
ctgcccacct gatgttatac ccaaagttga aggcactact atagcagatc aaatattacg    4380
atatggtagc ttagggggtgt tttttggagg tttaggcatt ggtacagggt cgggtacagg    4440
tggcaggact ggatatgtgc cccttggtag taccccaccg tctgaggcta tacctttaca    4500
gcccatacgt cccccagtta ccgttgatac tgtggggcct ttggattctt ctattgtatc    4560
tttaatagag gaatctagtt ttatagacgc cggtgcacca gccccatcaa ttcccactcc    4620
atctggtttt gatattacca cctctgcaga tactacacct gcaatactta atgtttcctc    4680
tattggagaa tcatctatac aaactgtttc tacacattta aatccctcct ttactgagcc    4740
atccgtactc cgcccctcctg cacctgcaga ggcctctgga catttaatat tttcctctcc    4800
tactgttagc acacatagtt atgaaaacat accaatggat acctttgtta tttctactga    4860
cagtggcaat gtcacgtcta gcacacccat tccagggtct cgccctgtgg cacgccttgg    4920
tttatacagt cgcaacaccc aacaagttaa ggttgttgac cctgcttttt taacatctcc    4980
tcatagactt gtaacatatg ataatccagc atttgaaggc tttaaccctg aggacacatt    5040
gcagtttcaa catagtgaca tatcgcctgc tcctgatcct gattttctag atattgttgc    5100
attacacaga cctgcattaa cctctcgcag gggtactgta cgttatagta gggttgggca    5160
aaaggctaca cttcgtactc gcagtggaaa gcaaataggg gctaaagtac attactacca    5220
agacttaagt cccatacagc ctgtccagga acaggtacaa cagcagcaac aatttgaatt    5280
acaatcttta aatacttctg tttctcccta tagtattaat gatggacttt atgatattta    5340
tgctgacgat gctgatacta tacatgattt tcagagtcct ctgcactcac atacgtcctt    5400
tgccaccaca cgtaccagta atgtgtccat accattaaat actggatttg acactcctct    5460
tgtgtcattg gaacctggtc cagacattgc atcttctgta acatctatgt ctagtccatt    5520
tattcctata tctccactaa ctccttttaa taccataatt gtggatggtg ctgattttat    5580
gttgcaccct agctatttta ttttgcgtcg cagacgtaaa cgttttccat attttttttgc    5640
agatgtccgt gtggcggcct agtgaggcca ctgtgtacct gcctcctgtg cctgtgtcta    5700
aggttgtaag cactgatgaa tatgtgtcac gcacaagcat ttattattat gctggcagtt    5760
ccagactttt ggctgttggc aatccatatt tttccatcaa aagtcccaat aacaataaaa    5820
aagtattagt tcccaaggta tcaggcttac agtatagggt ctttagggtg cgtttacctg    5880
atcccaataa atttggtttt cctgatacat cttttttataa ccctgataca caacgtttgg    5940
tctgggcatg tgtaggcctt gaaataggta ggggacagcc attgggtgtt ggcgtaagtg    6000
gtcatcctta tttaaataaa tttgatgaca ctgaaaccag taacagatat cccgcacagc    6060
cagggtctga taacagggaa tgcttatcta tggattataa acaaacacaa ttatgtttaa    6120
```

```
ttggctgtaa acctcccact ggtgagcatt ggggtaaagg tgttgcctgt aacaataatg    6180
cagctgctac tgattgtcct ccattggaac tttttaattc tattattgag gatggtgaca    6240
tggtagatac agggtttgga tgcatggact ttggtacatt gcaggctaat aaaagtgatg    6300
tgcctattga tatttgtaac agtacatgca aatatccaga ttatttaaaa atggccagtg    6360
aaccttatgg ggatagtttg ttctttttc ttagacgtga gcagatgttt gttagacact    6420
tttttaatag ggctggaaaa cttggcgagg ctgtcccgga tgacctttat attaaagggt    6480
ccggtaatac tgcagttatc caaagtagtg cattttttcc aactcctagt ggctctatag    6540
ttacctcaga atcacaatta tttaataagc cttattggct acagcgtgca caaggtcata    6600
acaatggcat ttgctggggc aatcagttat ttgttaccgt ggttgatacc actcgtagca    6660
ctaatatgac attatgcact gaagtaacta aggaaggtac atataaaaat gataatttta    6720
aggaatatgt acgtcatgtt gaagaatatg acttacagtt tgtttttcag ctttgcaaaa    6780
ttacactaac tgcagagata atgacatata tacatactat ggattccaat attttggagg    6840
actggcaatt tggtttaaca cctcctccgt ctgccagttt acaggacaca tatagatttg    6900
ttacctccca ggctattact tgccaaaaaa cagcaccccc taaagaaaag gaagatccat    6960
taaataaata tactttttgg gaggttaact taaaggaaaa gttttctgca gatctagatc    7020
agtttccttt gggacgaaag tttttattac aatcaggcct taaagcaaag cccagactaa    7080
aacgttcggc ccctactacc cgtgcaccat ccaccaaacg caaaaaggtt aaaaaataat    7140
tgttgtggta cttacactat tttattatac atgtttgttt gttttatgta tgtgttgtct    7200
gtttgtttat gtttgtgtat atgttgtatg tgttatgtgt catgtttgtg tacatgttct    7260
atgtccttgt cagtttcctg tttctgtata tatgtaataa actattgtgt gtattgtaaa    7320
ctatttgtat tgtttgggtg tatctatgag taaggtgctg tccctaaatt gccctaccct    7380
gccctgccta ttatgcatac ctatgtaata gtatttgtat gatatgtatt ttatagtttt    7440
taacagtact gcctccattt tactttacct ccattttgtg catgtaaccg atttcggttg    7500
ctggcacaaa cgtgtttttt ttaaactaca atttaaacaa tacagttaat cctttccctt    7560
cctgcactgc ttttgcctat acttgcatat gtgactcata tatacatgca gtgcagttgc    7620
aaaatgttta attatactca tagtttaaac atgcttatag gcacatattt taacttactt    7680
tcaatgctta agtgcagttt tggcttgcac aatagtttgt tatgccaaac tatgtcttgt    7740
aaaagtgact cactaacatt tattgccagg tgtggactaa ccgttttggg tcacattgtt    7800
catgtttcaa cattttatat aata                                            7824
```

METHOD FOR DETECTING CANCER CELL CAUSED BY HPV, METHOD FOR DETERMINING WHETHER OR NOT TISSUE IS AT STAGE OF HIGH-GRADE DYSPLASIA OR MORE SEVERE STAGE, AND PRIMER SET AND KIT USED THEREFOR

CROSS REFERENCE TO RELATED APPLICATIONS

This application is a National Stage of International Application No. PCT/JP2009/055337 filed Mar. 18, 2009, claiming priority based on Japanese Patent Application No. 2008-074267 filed Mar. 21, 2008, the contents of all of which are incorporated herein by reference in their entirety.

TECHNICAL FIELD

The present invention relates to a method for detecting a cancer cell caused by HPV, a method for determining whether or not a tissue is at a stage of high-grade dysplasia or a more severe stage, and a primer set and a kit used therefor.

BACKGROUND ART

A human papillomavirus (hereinafter referred to as "HPV") is a virus having circular double-stranded DNA as genome, which induces proliferative lesions. HPV is classified into 100 or more kinds of subtypes. Also, it is known that the subtypes of HPV share common regions, which are non-structural protein-coding E1 region, E2 region, E4 region, E5 region, E6 region and E7 region, capsid protein-coding L1 region and L2 region, and LCR.

HPV DNA has been detected in lesion sites of uterine cervical cancer and uterine cervical dysplasia, and tissues of oral cancer and pharyngeal cancer. Thus, HPV infection is regarded as one of the risk factors for uterine cervical cancer, oral cancer, and pharyngeal cancer. In most cases, a pattern of HPV infection is a transient infection in which HPV is spontaneously disappeared from a cell after a certain period of time from the establishment of infection. However, in 5 to 10% of HPV infections, there are cases where HPV is not disappeared and the infection turns into a persistent infection causing uterine cervical cancer.

It is to be noted that, in tissue diagnosis of uterine cervix, uterine cervical dysplasia is classified into three stages, namely mild-grade, moderate-grade, and high-grade dysplasia as a preliminary stage of generation of a cancer cell, depending on the degree of appearance of an atypical cell in the epithelium. When high-grade dysplasia is further aggravated, lesions of uterine cervical dysplasia reach a stage at which a cancer cell emerge in the epithelium. Then, uterine cervical dysplasia progresses to "intraepithelial carcinoma", in which cancer cells are confined to the epithelium, and "microinvasive squamous cell carcinoma" and "invasive squamous cell carcinoma", in which a cancer cell infiltrates from the epithelium down into subcutaneous tissues.

In most cases, lesions of mild-grade dysplasia or moderate-grade dysplasia are observed without particularly providing any treatment thereto. However, if a precursor lesion of high-grade dysplasia is left untreated, the lesion is highly likely to progress to invasive cancer. Thus, in many cases, treatment such as surgery is provided to a subject diagnosed as having high-grade dysplasia. Accordingly, determining whether or not a lesion in a subject is at a stage of high-grade dysplasia or a more severe stage is important in deciding a treatment method for the subject.

In chromosomal DNA in higher eukaryotes, among bases constituting DNA, the 5-position of cytosine is occasionally methylated. The methylation of DNA in higher eukaryotes functions as an inhibitory mechanism on the expression of genetic information. Recently, a report indicating that the presence or absence of methylation in HPV genomic DNA is strongly associated with onset of cancer has been made.

For example, Patent Document 1 describes that, when E6 region and LCR of HPV contained in a uterine cervical cell of a patient are not methylated, the presence of a uterine cervical cancer cell is more strongly indicated. However, there are cases where unmethylated E6 region and unmethylated LCR are detected in a cell other than a uterine cervical cancer cell. Thus, it is difficult to detect a cancer cell caused by HPV in uterine cervical cells of a patient with high accuracy only by confirming the methylation state of E6 region and LCR.

Also, Non-Patent Document 1 describes that, in uterine cervical cancer, L1 region is strongly methylated, whereas LCR and E6 region are not methylated in HPV-18. In Non-Patent Document 1, a nucleic acid that has been treated with a bisulfite salt, which corresponds to HPV-18 genomic DNA, is sequenced, and the methylation state thereof is confirmed. However, confirming methylation of DNA by sequencing is time-consuming and involves cumbersome operations. Thus, it is difficult to detect a cancer cell caused by HPV in a sample collected from a subject in a simple manner.

[Non-Patent Document 1] Tolga Turan et al., Virology 349 (2006) pp. 175-183

[Patent Document 1] National Publication of International Patent Application No. 2006-522607

DISCLOSURE OF THE INVENTION

An object of the present invention is to provide a method for detecting a cancer cell caused by HPV easily with high accuracy. Another object of the present invention is to provide a method for determining whether or not a tissue is at a stage of high-grade dysplasia or a more severe stage easily with high accuracy. Still another object of the present invention is to provide a primer set capable of detecting a cancer cell caused by HPV and determining whether or not a tissue is at a stage of high-grade dysplasia or a more severe stage easily with high accuracy. Yet still another object of the present invention is to provide a kit capable of diagnosing cancer caused by HPV easily with high accuracy. Yet still another object of the present invention is to provide a kit capable of diagnosing the stage of dysplasia.

That is, the present invention relates to the followings:

(1) A method for, detecting a cancer cell caused by HPV, comprising the steps of:

(A) preparing a sample containing DNA from a cell of a subject;

(B) converting unmethylated cytosine in DNA contained in the sample obtained in the step (A) into another base, to give a conversion sample;

(C) carrying out nucleic acid amplification reaction, by using the conversion sample obtained in the step (B), a first primer which hybridizes with a nucleic acid consisting of a nucleotide sequence in which cytosine present in a site other than a CpG site is converted into another base in a nucleotide sequence having a CpG site in L1 region or L2 region of HPV, and a second primer which hybridizes with a nucleic acid consisting of a nucleotide sequence in which cytosine is converted into another base in a nucleotide sequence having a CpG site in LCR or E6 region of HPV, wherein the nucleic acid amplification reaction is to amplify a nucleic acid consisting of a continuous nucleotide sequence ranged from the site with which the first primer is hybridized to the site with which the second primer is hybridized; and (D) detecting a cancer cell caused by HPV based on the result of the nucleic acid amplification reaction of the step (C);

(2) the method according to the above (1), wherein the step (A) comprises the steps of:

(a) mixing a solution containing a surfactant with a cell of a subject, to give a mixture;

(b) subjecting the mixture obtained in the step (a) to centrifugation, thereby precipitating an insoluble matter to give a supernatant; and (c) collecting the supernatant obtained in the step (b);

(3) the method according to the above (2), wherein the step (A) further comprises the step of:

(a1) subjecting the mixture obtained in the step (a) to a physical treatment, thereby liberating DNA from the cell, between the step (a) and the step (b), wherein, in the step (b), a product obtained in the step (a1) is subjected to centrifugation, thereby precipitating an insoluble matter, to give a supernatant;

(4) a method for determining whether or not a tissue is a tissue at a stage of high-grade dysplasia or a more severe stage, comprising the steps of:

(A) preparing a sample containing DNA from a tissue of a subject;

(B) converting unmethylated cytosine in DNA contained in the sample obtained in the step (A) into another base, to give a conversion sample;

(C) carrying out nucleic acid amplification reaction, by using the conversion sample obtained in the step (B), a first primer which hybridizes with a nucleic acid consisting of a nucleotide sequence in which cytosine present in a site other than a CpG site is converted into another base in a nucleotide sequence having a CpG site in L1 region or L2 region of HPV, and a second primer which hybridizes with a nucleic acid consisting of a nucleotide sequence in which cytosine is converted into another base in a nucleotide sequence having a CpG site in LCR or E6 region of HPV, wherein the nucleic acid amplification reaction is to amplify a nucleic acid consisting of a continuous nucleotide sequence ranged from the site with which the first primer is hybridized to the site with which the second primer is hybridized; and (D) determining whether or not the tissue is a tissue at a stage of high-grade dysplasia or a more severe stage based on the result of the nucleic acid amplification reaction of the step (C);

(5) the method according to the above (4), wherein the tissue is a uterine cervical tissue;

(6) a primer set comprising:

a first primer which hybridizes with a nucleic acid consisting of a nucleotide sequence in which cytosine present in a site other than a CpG site is converted into another base in a nucleotide sequence having a CpG site in L1 region or L2 region of HPV; and a second primer which hybridizes with a nucleic acid consisting of a nucleotide sequence in which cytosine is converted into another base in a nucleotide sequence having a CpG site in LCR or E6 region of HPV, wherein the primer set is used to amplify a nucleic acid consisting of a continuous nucleotide sequence ranged from the site with which the first primer is hybridized to the site with which the second primer is hybridized by nucleic acid amplification reaction, among nucleic acids each consisting of nucleotide sequence of HPV genomic DNA in which unmethylated cytosine is converted into another base.

(7) the primer set according to the above (6), wherein the first primer is a primer which hybridizes with a nucleic acid consisting of a nucleotide sequence in which cytosine present in a site other than a CpG site is converted into another base in a nucleotide sequence having a CpG site in L1 region of HPV.

(8) the primer set according to the above (6), wherein the second primer is a primer which hybridizes with a nucleic acid consisting of a nucleotide sequence in which cytosine is converted into another base in a nucleotide sequence having a CpG site in LCR of HPV.

(9) the primer set according to the above (6), wherein the another base is uracil or thymine;

(10) the primer set according to the above (6), wherein the first primer and the second primer are primers used for amplifying a nucleic acid by a polymerase chain reaction method, a strand displacement amplification method, a ligase chain reaction method, on a transcriptional amplification method;

(11) a diagnostic kit for a cancer caused by HPV comprising; the primer set of the above (6), and an unmethylated cytosine-conversion agent for converting unmethylated cytosine in a nucleic acid into another base;

(12) the diagnostic kit according to the above (11), wherein the unmethylated cytosine-conversion agent is a bisulfite salt;

(13) the diagnostic kit according to the above (11), wherein the cancer caused by HPV is uterine cervical cancer, oral cancer, or pharyngeal cancer; as well as,

(14) a diagnostic kit for a stage of dysplasia comprising; the primer set of the above (6), and an unmethylated cytosine-conversion agent for converting unmethylated cytosine in a nucleic acid into another base.

BEST MODE FOR CARRYING OUT THE INVENTION

Figure 1:
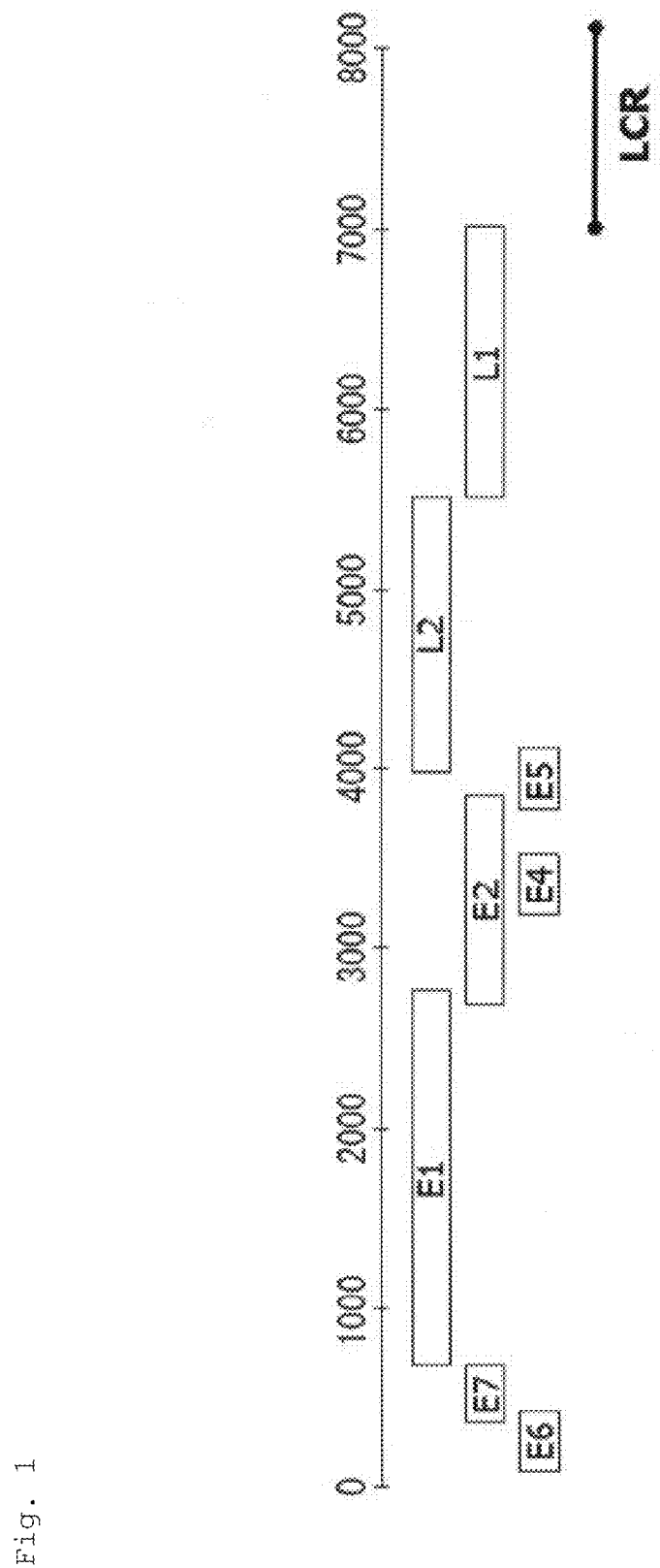
FIG. 1 is a schematic illustrative diagram of the genetic structure of HPV.

The primer set of the present invention contains a first primer which hybridizes with, in a nucleotide sequence having a CpG site in L1 region or L2 region of HPV (also referred to as "first nucleotide sequence"), a nucleic acid consisting of a nucleotide sequence in which cytosine present in a site other than a CpG site is converted into another base (also referred to as "second nucleotide sequence"), and a second primer which hybridizes with, in a nucleotide sequence having a CpG site in LCR or E6 region of HPV (also referred to as "third nucleotide sequence"), a nucleic acid consisting of a nucleotide sequence in which cytosine is converted into another base (also referred to as "fourth nucleotide sequence"). The primer set is used to amplify, among nucleic acids including nucleotide sequences obtained by converting unmethylated cytosine into another base, which correspond to HPV genomic DNA, a nucleic acid consisting of a continuous nucleotide sequence from a site with which the first primer hybridizes to a site with which the second primer hybridizes by nucleic amplification reaction. The second nucleotide sequence is a nucleotide sequence of a nucleic acid resulting from conversion of a nucleic acid including the first nucleotide sequence, and the second nucleotide sequence corresponds to the first nucleotide sequence except that cytosine present in a site other than a CpG site has been converted into another base. Also, the fourth nucleotide sequence is a nucleotide sequence of a nucleic acid resulting from conversion of a nucleic acid including the third nucleotide sequence, and it corresponds to the third nucleotide sequence except that all of cytosine has been converted into another base.

One of the significant features of the primer set of the present invention is that the primer set contains the first primer which hybridizes with a nucleic acid consisting of a nucleotide sequence in which cytosine present in a site other than a CpG site is converted into another base in a nucleotide sequence having a CpG site in L1 region or L2 region of HPV, and the second primer which hybridizes with a nucleic acid consisting of a nucleotide sequence in which cytosine is converted into another base in a nucleotide sequence having a CpG site in LCR or E6 region of HPV.

In HPV genomic DNA contained in a cancer cell caused by HPV, cytosine in a CpG site in L2 region or L1 region is methylated, and cytosine in a CpG site in LCR or E6 region is unmethylated. Thus, using the primer set of the present invention for nucleic acid amplification reaction, a nucleic acid consisting of a nucleotide sequence in which unmethylated cytosine is converted into another base, which corresponds to genomic DNA of canceration-causing HPV, can be specifically amplified. As described above, according to the primer set of the present invention, a cancer cell caused by HPV can be easily detected with high accuracy. Therefore, according to the primer set of the present invention, diagnosis of uterine cervical cancer, oral cancer, and pharyngeal cancer can be easily carried out with high accuracy.

Further, in HPV genomic DNA present in lesions at a stage of high-grade dysplasia or a more severe stage, cytosine in a CpG site in L2 region or L1 region is methylated, and cytosine in a CpG site in LCR or E6 region is unmethylated. Thus, using the primer set of the present invention for nucleic acid amplification reaction, a nucleic acid consisting of a nucleotide sequence in which unmethylated cytosine is converted into another base, which corresponds to HPV genomic DNA present in lesions at a stage of high-grade dysplasia or a more severe stage, can be specifically amplified. Therefore, according to the primer set of the present invention, stage of dysplasia can be easily diagnosed with high accuracy. Also, according to the primer set of the present invention, whether or not a tissue is at a stage of high-grade dysplasia or a more severe stage can be easily determined with high accuracy.

As used herein, a cancer cell caused by HPV refers to a cell that has become cancerous or is at a high risk of becoming cancerous due to HPV infection. More specifically, a cancer cell caused by HPV refers to an HPV-infected cell causing onset of uterine cervical cancer, oral cancer or pharyngeal cancer, a uterine cervical cancer cell, an oral cancer cell, or a pharyngeal cancer cell.

As used herein, "a stage of high-grade dysplasia or a more severe stage" refers to the stage of cancer that is classified into "high-grade dysplasia" or a more severe stage, namely "intraepithelial carcinoma", "microinvasive squamous cell carcinoma", or "invasive squamous cell carcinoma", according to the classification based on "The General Rules for Clinical and Pathological Management of Uterine Cervical Cancer 1997" edited by Japan Society of Obstetrics and Gynecology. When lesions in tissues are determined to be at the above stages, in most cases a subject requires treatment such as surgery. Thus, the determination of whether or not a tissue is at a stage of high-grade dysplasia or a more severe stage is crucial in the clinical practice. On the other hand, lesions that are milder than "high-grade dysplasia" are classified into lesions at a stage of "no abnormality in the epithelium", "mild-grade dysplasia", or "moderate-grade dysplasia". When lesions are at the above stages, in most cases a subject is observed without receiving any particular treatment.

As used herein, "an abnormal cell" refers to "an atypical cell" and "a cancer cell". Herein, "an atypical cell" refers to a cell that is not a cancer cell but has abnormal nuclei such as enlarged nuclei, increased chromatin, and irregularly-shaped nuclei.

As described above, a cancer cell caused by HPV has HPV genomic DNA in which cytosine in a CpG site in L2 region or L1 region is methylated, and cytosine in a CpG site in LCR or E6 region is unmethylated. When HPV genomic DNA contained in the cancer cell caused by HPV is treated with an unmethylated cytosine-conversion agent that converts unmethylated cytosine into another base, cytosine in a CpG site in L2 region or L1 region is not converted into another base, whereas cytosine in a CpG site in LCR or E6 region is converted into another base. Accordingly, the use of the primer set of the present invention enables amplification of, among HPV genomic DNA that has been treated with an unmethylated cytosine-conversion agent, only a nucleic acid in which a CpG site in L2 region or L1 region remains to be a nucleotide sequence of a dinucleotide including cytosine and guanine, while cytosine in a CpG site in LCR or E6 region is converted into another base by nucleic acid amplification reaction.

Further, in the primer set of the present invention, the first primer hybridizes with a nucleic acid consisting of a nucleotide sequence in which cytosine present in a site other than a CpG site is converted into another base in a nucleotide sequence having a CpG site in L1 region or L2 region of HPV. Also, the second primer hybridizes with a nucleic acid consisting of a nucleotide sequence in which cytosine is converted into another base in a nucleotide sequence having a CpG site in LCR or E6 region of HPV. Thus, the primer set of the present invention enables amplification of a nucleic acid that has been treated with an unmethylated cytosine-conversion agent, which corresponds to DNA of a continuous region containing at least a part of L2 region or L1 region and at least a part of LCR or E6 region in HPV genomic DNA, which causes HPV-infected cells to become cancerous, by single nucleic acid amplification reaction.

HPV is a virus containing approximately 8 kb of circular DNA. The HPV includes, for example, HPV16, HPV18, HPV31, HPV33, HPV35, HPV39, HPV45, HPV51, HPV52, HPV56, HPV58, HPV59, HPV68, HPV73, HPV82 and the like.

As shown in FIG. 1, HPV genome has open reading frames of early genes encoding nonstructural proteins (E1 region, E2 region, E4 region, E5 region, E6 region and E7 region), open reading frames of late genes encoding capsid proteins (L1 region and L2 region), and a gene region of LCR. E1 region is a region associated with replication of viral genome. E2 region is a region associated with regulation of viral transcription. E5 region, E6 region, and E7 region are regions associated with canceration. E6 region is a region encoding proteins that bind to p53, which is an antioncogene, thereby promoting degradation of p53. E7 region is a region encoding a protein that binds to Rb, which is an antioncogene, thereby inactivating Rb. L1 region and L2 region are regions associated with capsid formation. Long control region (LCR) is a region associated with regulation of viral gene expression.

Figure 2:
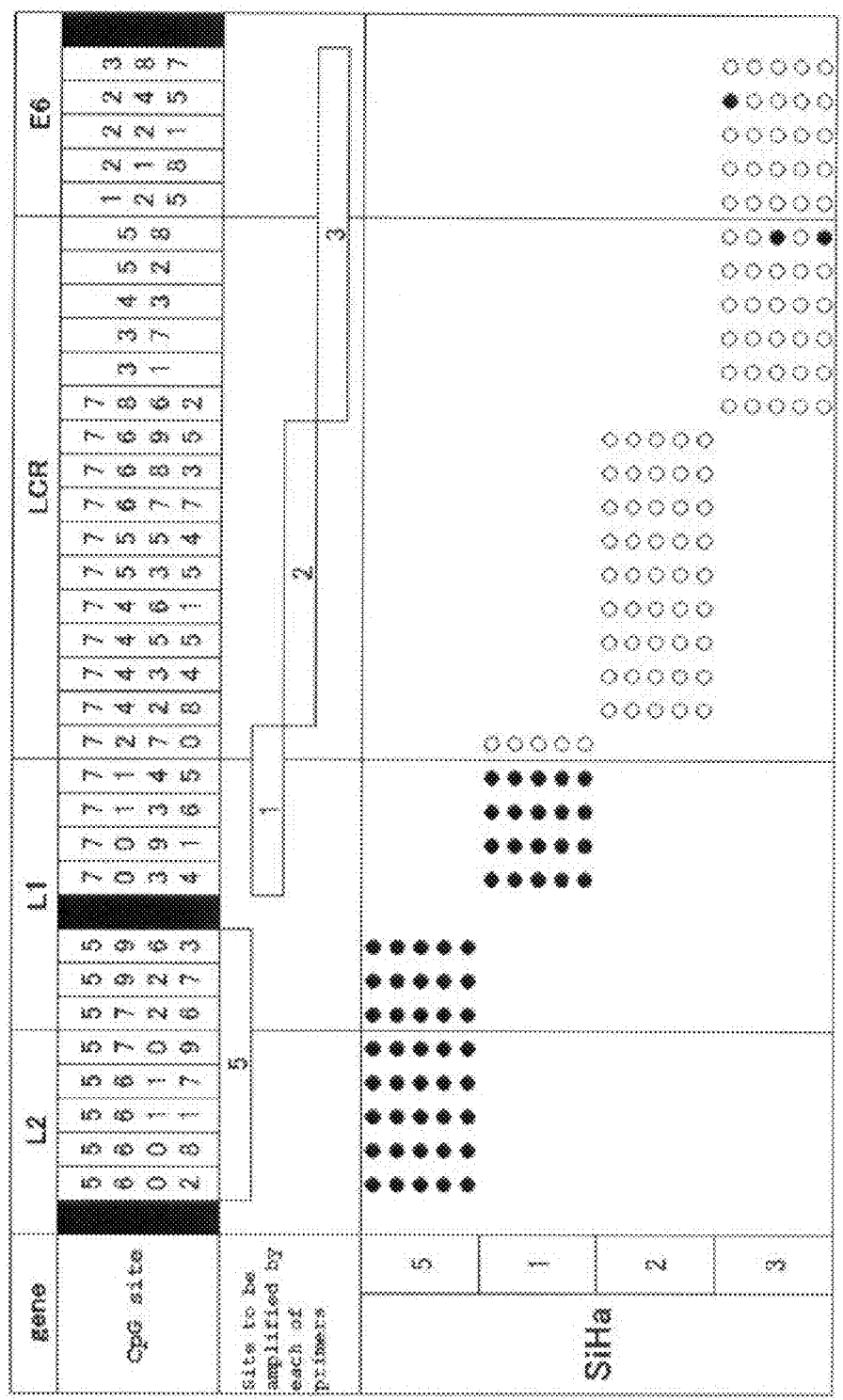
FIG. 2 is a schematic diagram showing methylated CpG sites and unmethylated CpG sites in HPV16 genomic DNA integrated into a SiHa cell.

Generally, when HPV infects and invades a cell, cytosine in a certain CpG site among CpG sites in HPV genomic DNA are methylated by DNA methylation mechanism of a living body. Especially, as shown in FIG. 2, in HPV in a uterine cervical cancer cell, cytosine in CpG sites in L1 region and L2 region is methylated, whereas cytosine in CpG sites in LCR and E6 region is unmethylated.

Table 1 shows the methylation state of CpG sites in L1 region and L2 region as well as LCR and E6 region in HPV genomic DNA contained in an HPV-infected cell. Herein, among the HPV-infected cells shown in Table 1, HPV-infected cell 2 indicates a cancer cell caused by HPV. It is to be noted that, in Table 1, "methylated" indicates that cytosine in a CpG site is methylated, whereas "unmethylated" indicates that cytosine in a CpG site is unmethylated.

TABLE 1

| | Methylation of HPV genomic DNA | |
|---|---|---|
| | L1 or L2 | LCR or E6 |
| HPV-infected cell 1 | Methylated | Methylated |
| HPV-infected cell 2 | Methylated | Unmethylated |
| HPV-infected cell 3 | Unmethylated | Methylated |
| HPV-infected cell 4 | Unmethylated | Unmethylated |

As described above, methylation of DNA is detected in CpG sites in L1 region and L2 region in HPV in a uterine cervical cancer cell. However, as shown in Table 1, there are cases where methylation of DNA in L1 region or L2 region are observed also in an HPV-infected cell that is not a cancer cell caused by HPV. Thus, when only methylation in L1 region or L2 region is used as an index for detection of a cancer cell caused by HPV, there are cases where it is difficult to distinguish a cancer cell caused by HPV from other HPV-infected cells. That is, when only methylation in L1 region or L2 region is used as an index for detection of a cancer cell caused by HPV, in some cases not only HPV-infected cell 2 shown in Table 1, which indicates a cancer cell caused by HPV, but also HPV-infected cell 1 may be detected.

Further, CpG sites in LCR and E6 region in HPV in a uterine cervical cancer cell are unmethylated. However, there are cases where CpG sites in LCR or E6 region are unmethylated also in an HPV-infected cell and the like that is not a cancer cell caused by HPV. Thus, when only the state of unmethylation in LCR or E6 region is used as an index for detection of a cancer cell caused by HPV, there are cases where it is difficult to distinguish a cancer cell caused by HPV from other HPV-infected cells. That is, when only the state of unmethylation in LCR or E6 region is used as an index for detection of a cancer cell caused by HPV, in some cases not only HPV-infected cell 2 shown in Table 1, which indicates a cancer cell caused by HPV, but also HPV-infected cell 4 may be detected.

However, the primer set of the present invention enables specific amplification of a nucleic acid that has been treated with an unmethylated cytosine-conversion agent, which corresponds to HPV genomic DNA contained in HPV-infected cell 2 shown in Table 1, by nucleic acid amplification reaction. Thus, with use of the primer set of the present invention, an excellent effect is exerted that HPV-infected cell 2, which indicates a cancer cell caused by HPV, can be specifically detected from among HPV-infected cells 1 to 4 shown in Table 1.

On the other hand, also in HPV contained in a tissue at a stage of high-grade dysplasia or a more severe stage, cytosine in CpG sites in L1 region and L2 region is methylated, whereas cytosine in CpG sites in LCR and E6 region is unmethylated. Accordingly, with use of the primer set of the present invention, an excellent effect is exerted that HPV DNA in a tissue at a stage of high-grade dysplasia or a more severe stage can be specifically detected.

As used herein, "a primer hybridizes" means that a primer hybridizes with a nucleic acid under stringent conditions. The state where a primer has hybridized with a nucleic acid is a state where the primer is annealed to a complementary sequence in a nucleic acid in a state suitable for carrying out nucleic acid amplification reaction. Herein, the stringent conditions refer to the conditions that are generally used by those skilled in the art when hybridization of polynucleotide is carried out. The stringent conditions are not particularly limited, as long as it is a condition under which the primer set of the present invention can hybridize with a nucleic acid having a nucleotide sequence of interest in a nucleic acid that has been treated with an unmethylated cytosine-conversion agent, which corresponds to HPV genomic DNA. The stringency in hybridization is known as a function of temperature, salt concentration, length of primer, GC content in a nucleotide sequence of primer, and concentration of chaotropic agent in a hybridization buffer. As the stringent conditions, for example, the conditions set forth in Sambrook, J. et al. (1998) Molecular Cloning: A Laboratory Manual (2nd ed.), Cold Spring Harbor Laboratory Press, New York and the like can be used.

It is to be noted that "another base" includes uracil and thymine. For example, when a bisulfite salt is used as an unmethylated cytosine-conversion agent, unmethylated cytosine is converted into uracil. Also, uracil thus converted will be converted into thymine by nucleic acid amplification reaction using the primer set of the present invention.

The first primer and the second primer are primers used to amplify a nucleic acid by nucleic acid amplification. Specifically, the first primer and the second primer are preferably primers each used to amplify a nucleic acid by a polymerase chain reaction method, a strand displacement amplification method, a ligase chain reaction method, or a transcriptional amplification method. Thus, by carrying out nucleic acid amplification reaction with the primer set of the present invention, using as a template DNA which has been extracted from a cell of a subject and has been treated with an unmethylated cytosine-conversion agent, a subject having a cancer cell caused by HPV and a tissue at a stage of high-grade dysplasia or a more severe stage can be easily confirmed based on the results of the amplification reaction.

The polymerase chain reaction method can be carried out in accordance with a conventional technique. The strand displacement amplification method includes, for example, LAMP method, ICAN (trademark) method, SMAP method and the like. The transcriptional amplification method includes, for example, TAS method and the like.

The primer set of the present invention can be produced by the known method, depending on the kind of nucleic acid amplification method to be employed. More specifically, regarding each of a nucleotide sequence of L1 region or L2 region and a nucleotide sequence of LCR or E6 region, a nucleotide sequence after treatment with an unmethylated cytosine-conversion agent is predicted. Subsequently, the primer set of the present invention can be produced by designing a nucleotide sequence of each primer in the primer set of the present invention with a commercially available primer design software and the like based on the nucleotide sequence thus predicted, and synthesizing each primer. The software used to design each primer of the primer set used for real-time PCR, which is polymerase chain reaction method, includes, for example, GENETYX, primer 3 and the like. Also, the software used to design each primer of the primer set used for LAMP method, which is strand displacement amplification, includes, for example, Primer Explorer and the like.

Since a cancer cell caused by HPV can be detected as described above according to the primer set of the present invention, cancer caused by HPV can be diagnosed. Accordingly, the present invention encompasses a diagnostic kit for cancer caused by HPV (hereinafter, also referred to as "diagnostic kit 1").

The diagnostic kit 1 of the present invention is a kit containing the primer set and an unmethylated cytosine-conversion agent that converts unmethylated cytosine, in a nucleic acid into another base.

The unmethylated cytosine-conversion agent may be an agent, for converting unmethylated cytosine in a nucleic acid into another base, and examples thereof include a bisulfite salt and the like. The bisulfite salt includes, for example, sodium bisulfite and the like.

In the diagnostic kit 1 of the present invention, the primer set is dissolved in a solvent such as buffer suitable for stably maintaining nucleic acid, and is provided in a sealed container and the like suitable for stably maintaining nucleic acid. Also, the unmethylated cytosine-conversion agent is dissolved in a solvent suitable for dissolving the unmethylated cytosine-conversion agent, and is provided in a sealed, appropriate container and the like.

The cancer caused by HPV to which the diagnostic kit 1 of the present invention is applicable includes, for example, uterine cervical cancer, oral cancer, pharyngeal cancer and the like.

According to the primer set of the present invention, a cancer cell caused by HPV can be detected as described above. The present invention also encompasses a method for detecting a cancer cell caused by HPV.

The method for detecting a cancer cell of the present invention includes the steps of:
(A) preparing a sample containing DNA from a cell of a subject;
(B) converting unmethylated cytosine in DNA contained in the sample obtained in the step (A) into another base, to give a conversion sample;
(C) carrying out nucleic acid amplification reaction, by using the conversion sample obtained in the step (B), a first primer which hybridizes with a nucleic acid consisting of a nucleotide sequence in which cytosine present in a site other than a CpG site is converted into another base in a nucleotide sequence having a CpG site in L1 region or L2 region of HPV, and a second primer which hybridizes with a nucleic acid consisting of a nucleotide sequence in which cytosine is converted into another base in a nucleotide sequence having a CpG site in LCR or E6 region of HPV, wherein the nucleic acid amplification reaction is to amplify a nucleic acid consisting of a continuous nucleotide sequence ranged from the site with which the first primer is hybridized to the site with which the second primer is hybridized; and
(D) detecting a cancer cell caused by HPV based on the result of the nucleic acid amplification reaction of the step (C).

The method for detecting a cancer cell of the present invention can be easily carried out by, for example, using the diagnostic kit for a cancer caused by HPV.

In the method for detecting a cancer cell of the present invention, a sample containing DNA is prepared from a cell of a subject (step (A)).

In the step (A), preparation of a sample containing DNA from a cell of a subject can be carried out by the known method and the like. For example, preparation of the sample containing DNA can be carried out by the steps of:
(a) mixing a solution containing a surfactant with a cell of a subject, to give a mixture;
(b) subjecting the mixture obtained in the step (a) to centrifugation, thereby precipitating an insoluble matter to give a supernatant; and
(c) collecting the supernatant obtained in the step (b).

By carrying out the above steps (a) to (c) in the step (A), DNA can be extracted from cells of a subject and a sample containing the DNA can be prepared.

Further, the step (A) may further include a step (a1) of subjecting the mixture obtained in the step (a) to a physical treatment, thereby isolating DNA from the cell, between the step (a) and the step (b). In the above case, in the step (b), a product obtained in the step (a1) is subjected to centrifugation, thereby precipitating an insoluble matter to give a supernatant.

The surfactant includes, for example, sodium dodecyl sulfate (SDS), sodium tetradecyl sulfate, sodium dodecyl sulfonate, sodium tetradecyl sulfonate, sodium cholate (CHO), sodium deoxycholate (DOC), sodium taurocholate, sodium taurodeoxycholate and the like. Sodium dodecyl sulfate (SDS) is particularly preferable. Also, as a method of physical treatment, the known method for disrupting physically a cell can be used. Examples thereof include a method for disrupting a cell with a homogenizer and a method for disrupting a cell by shaking the cell with a mixer. A commercially available kit for extraction of DNA can be used in the preparation of a sample containing DNA.

DNA extracted as above can be dissolved in water or buffer, and provided as a DNA solution. Water and buffer for dissolving DNA are preferably those capable of stably maintaining dissolved DNA. The water and buffer for dissolving DNA includes, for example, PCR-grade water free from nucleases, TE solution (10 mM Tris-HCl buffer (pH 8.0), 1 mM EDTA) and the like.

The cell of a subject may be a target cell for HPV infection or a target cell for HPV latent infection. The cell of a subject is not particularly limited. The cell includes, for example, a mucosal cell and a skin cell. The mucosa includes, for example, the mucosa of the inner wall of a hollow organ such as genitourinary apparatus, digestive organ, respiratory apparatus and the like. More specific examples of the mucosa include uterine cervical mucosa, oral and pharyngeal mucosa and the like. Among the cell of a subject, a uterine cervical cell and an oral and pharyngeal cell are preferable. According to the detection method of the present invention, by using a uterine cervical cell or a oral and pharyngeal cell as the cell of a subject; a cancer cell caused by HPV causing onset of uterine cervical cancer, oral cancer, or pharyngeal cancer can be detected. The uterine cervical cell is a cell collectable from the uterine cervix (for example, uterine cervical mucosa and the like) of a subject. Also, the oral and pharyngeal cell is a cell collectable from the oral cavity and pharynx (for example, oral and pharyngeal mucosa) of a subject.

Subsequently, unmethylated cytosine in DNA contained in the sample obtained in the step (A) is converted into another base (step (B)).

Conversion of unmethylated cytosine into another base can be carried out by using the unmethylated cytosine-conversion agent. When a bisulfite salt is used as the unmethylated cytosine-conversion agent, methylated cytosine is not converted, whereas unmethylated cytosine is converted into uracil as described above. The bisulfite salt includes, for example, sodium bisulfite and the like. When sodium bisulfite, which is a bisulfite salt, is used as the unmethylated cytosine-conversion agent, conversion of unmethylated cytosine into another base can be carried out by adding 10 M sodium bisulfite solution to a sample containing DNA, and incubating the mixture thus obtained under appropriate temperature conditions.

Subsequently, using the conversion sample obtained in the step (B), the first primer which hybridizes with a nucleic acid consisting of a nucleotide sequence in which cytosine present in a site other than a CpG site is converted into another base in a nucleotide sequence having a CpG site in L1 region or L2 region of HPV, and the second primer which hybridizes with a nucleic acid consisting of a nucleotide sequence in which cytosine is converted into another base in a nucleotide sequence having a CpG site in LCR or E6 region of HPV, nucleic acid amplification reaction is carried out to amplify a nucleic acid including a continuous nucleotide sequence from a site with which the first primer hybridizes to a site with which the second primer hybridizes (step (C)). Because nucleic acid amplification reaction is carried out using the conversion sample, the first primer and the second primer in the step (C) in the detection method of the present invention, a nucleic acid in which unmethylated cytosine is converted into another base, which corresponds to genomic DNA of cancerivation-causing HPV, can be specifically amplified. Therefore, according to the detection method of the present invention, a cancer cell caused by HPV can be detected with high accuracy.

The nucleic acid amplification reaction is carried out by the polymerase chain reaction method, the strand displacement amplification method, the ligase chain reaction method, or the transcriptional amplification method as described above. Among them, the polymerase chain reaction method is preferable.

In the nucleic acid amplification reaction using the primer set, an amplification product will be obtained when HPV genomic DNA in which cytosine in a CpG site in L2 region or L1 region is methylated, and cytosine in a CpG site in LCR or E6 region is unmethylated is present in the sample containing DNA that has been treated with the above-described unmethylated cytosine-conversion agent. That is, an amplification product will be obtained when HPV genomic DNA shown as HPV-infected cell 2 in Table 1 is present in the sample containing DNA of the cell of a subject. On the other hand, an amplification product will not be obtained when only HPV genomic DNA shown as an HPV-infected cell 1, 3 and 4 as shown in Table 1 are present in the sample containing DNA of the cell of a subject.

Subsequently, a cancer cell caused by HPV is detected based on the results of the nucleic acid amplification reaction in the step (C) (step (D)). The subject is determined to have a cancer cell caused by HPV when an amplification product is obtained by nucleic acid amplification reaction. That is, the presence of the amplification product could be an index indicating that the subject has persistent HPV infection. On the other hand, the subject is determined not to have a cancer cell caused by HPV when an amplification product is not obtained by nucleic acid amplification reaction. In this case, the absence of the amplification product could be an index indicating that the subject is not infected with HPV or, even if the subject is infected with HPV, the subject has a transient infection. As shown above, in the detection method of the present invention, the presence of the amplification product can be easily detected by confirming a cancer cell caused by HPV.

Whether or not an amplification product has been obtained by nucleic acid amplification reaction can be confirmed by the known method. The method includes, for example, an agarose gel electrophoresis method, a method including hybridizing a labeling probe to an amplification product to detect the resultant, a method for detecting fluorescence using an intercalator capable of binding to double-stranded DNA (for example, SYBRGreen and the like), and a method for detecting turbidity caused by a byproduct generated by nucleic acid amplification.

Also, the primer set of the present invention enables determination of whether or not a tissue obtained by a subject is at a stage of high-grade dysplasia or a more severe stage, and also enables diagnosis of the stage of dysplasia. Accordingly, the present invention also encompasses a diagnostic kit for a stage of dysplasia (hereinafter, also referred to as "diagnostic kit 2").

The diagnostic kit 2 of the present invention is a kit containing the primer set and the unmethylated cytosine-conversion agent. In the diagnostic kit 2 of the present invention, the primer set and the unmethylated cytosine-conversion agent are provided in a form similar to the diagnostic kit 1.

The tissue of a subject to which the diagnostic kit 2 of the present invention is applicable may be a tissue containing a target cell for HPV infection or a tissue containing a target cell for HPV latent infection. The tissue includes, for example, a tissue collected from uterine cervix, or oral cavity and pharynx. It is particularly preferable to apply the diagnostic kit 2 to diagnose a tissue collected from the uterine cervix.

Further, as described above, according to the primer set of the present invention, whether or not a tissue of a subject is at a stage of high-grade dysplasia or a more severe stage can be determined. The present invention also encompasses a method for determining whether or not a tissue is at a stage of high-grade dysplasia or a more severe stage.

The determination method of the present invention includes the steps of:
(A) preparing a sample containing DNA from a tissue of a subject;
(B) converting unmethylated cytosine in DNA contained in the sample obtained in the step (A) into another base, to give a conversion sample;
(C) carrying out nucleic acid amplification reaction, by using the conversion sample obtained in the step (B), a first primer which hybridizes with a nucleic acid consisting of a nucleotide sequence in which cytosine present in a site other than a CpG site is converted into another base in a nucleotide sequence having a CpG site in L1 region or L2 region of HPV, and a second primer which hybridizes with a nucleic acid consisting of a nucleotide sequence in which cytosine is converted into another base in a nucleotide sequence having a CpG site in LCR or E6 region of HPV, wherein the nucleic acid amplification reaction is to amplify a nucleic acid consisting of a continuous nucleotide sequence ranged from the site with which the first primer is hybridized to the site with which the second primer is hybridized; and (D) determining whether or not the tissue is at a stage of high-grade dysplasia or a more severe stage based on the result of the nucleic acid amplification reaction of the step (C).

In the determination method of the present invention, a sample containing DNA is prepared from a tissue of a subject (step (A)).

In the step (A) of the detection method, preparation of a sample containing DNA from a tissue of a subject may be carried by the known method and the like. Also, a sample containing DNA can be prepared from a tissue of a subject by the same operations as in the preparation of a sample containing DNA from a cell of a subject in the step (A) of the method for detecting a cancer cell caused by HPV.

The tissue of a subject may be a tissue containing a target cell for HPV infection or a target cell for HPV latent infection. Specific examples of the tissue of a subject include a tissue collected from the uterine cervix, or oral cavity and pharynx of a subject.

The step (B) and step (C) in the determination method of the present invention can be carried out by the same operations as in the step (B) and step (C) in the method for detecting a cancer cell caused by HPV. Because nucleic acid amplification reaction is carried out using the conversion sample obtained in the step (B), the first primer, and the second primer in the step (C) in the determination method of the present invention, a nucleic acid in which unmethylated cytosine is converted into another base, which corresponds to HPV genomic DNA present in a lesion at a stage of high-grade dysplasia or a more severe stage, can be specifically amplified. Therefore, according to the determination method of the present invention, whether or not a tissue is at a stage of high-grade dysplasia or a more severe stage can be determined with high accuracy.

Subsequently, in the determination method of the present invention, whether or not the tissue is at a stage of high-grade dysplasia or a more severe stage. On the contrary, when an amplification product is not obtained by the nucleic acid amplification reaction, the tissue of a subject is determined not to be at a stage of high-grade dysplasia or a more severe stage. As described above, in the determination method of the present invention, whether or not a tissue is at a stage of high-grade dysplasia or a more severe stage is easily determined by confirming the presence or absence of an amplification product, using the presence or absence of the amplification product as an index.

Hereinafter, the present invention will be described in detail based on Examples, but the present invention is not limited thereto.

EXAMPLES

Experimental Example 1

To 1 μg of genomic DNA of a SiHa cell, which is a cell line derived from uterine cervical cancer having HPV16 genome integrated into its chromosome, 300 μL of 0.3 M sodium hydroxide solution was added, followed by incubation at 37° C. for 10 minutes. Subsequently, 300 μL of 10 M bisulfite salt solution (10 M sodium bisulfite solution) was added to the resulting product, followed by incubation at 80° C. for 40 minutes to carry out bisulfite salt treatment of the genomic DNA. DNA contained in the resulting solution after the bisulfite salt treatment was purified by a DNA purification kit (manufactured by QIAGEN under the trade name of Qiaquick PCR purification kit). To DNA thus purified, sodium hydroxide was added so as to have a final concentration of 0.3 M, followed by incubation at room temperature for 5 minutes. Thereafter, the product thus obtained was purified by a spin column for nucleic acid purification (manufactured by GE Healthcare under the trade name of MicroSpin S-300 HR Columns), to give an analytical sample.

To 2 μL of the analytical sample, 2.5 μL of reagent (×10 buffer) contained in a PCR reagent (manufactured by TAKARA BIO INC. under the trade name of TaKaRa EX Taq (trademark) Hot Start Version), 0.125 μL of DNA polymerase (trade name: TaKaRa Ex Taq HS (5 U/μL)), 2 μL of 2.5 mM dNTP mixture, 1 μL of an aqueous solution of forward primer (10 mM), 1 μL of an aqueous solution of reverse primer (10 mM), and 16.38 μL of water were added to prepare a PCR reaction liquid.

A primer set consisting of the forward primer and the reverse primer and PCR thermal profile used are shown in Table 2.

TABLE 2

| Primer | Nucleotide sequence | SEQ ID No. | Tm (° C.) | Thermal profile of PCR |
|---|---|---|---|---|
| 1F(16) | 5'-GGTTTATAATTTTTTTAGGAGGTATATTAGAAGA-3' | 1 | 62.67 | (1) |
| 1R(16) | 5'-ATTACATAACACAATAATTACACAAACATTTAAAA-3' | 2 | 63 | |
| 2F(16) | 5'-TTAATATTTATTAATTGTGTTGTGGTTATTTATTG-3' | 3 | 62.57 | (2) |
| 2R(16) | 5'-TAACCTTAAAAATTTAAACCTTATACCAAATATAC-3' | 4 | 61.7 | |
| 3F(16) | 5'-TATTGTTTATTTGTAAAATTGTATATGGGTGTGT-3' | 5 | 65.05 | (1) |
| 3R(16) | 5'-ATATCTTTACTTTTCTTCAAAACACAATAACTTT-3' | 6 | 63.11 | |
| 5F(16) | 5'-TTGTTGATGTAGGTGATTTTTATTTATATTTTAGTT-3' | 7 | 64 | (1) |
| 5R(16) | 5'-CCACTAATACCCACACCTAATAACTAACC-3' | 8 | 64.12 | | dysplasia or a more severe stage is determined based on the results of the nucleic acid amplification reaction in the nucleic acid amplification step (step (D)). When an amplification product is obtained by the nucleic acid amplification reaction, the tissue of a subject is determined to be at a stage of high- In Table 2, PCR thermal profile (1) represents conditions for carrying out the reaction of incubation at 95° C. for 4.5 minutes followed by 40 cycles of reactions, each cycle being 95° C. for 30 seconds, 60° C. for 30 seconds, and 72° C. for 40 seconds. Also, in Table 2, PCR thermal profile (2) represents conditions for carrying out the reaction of incubation at 95° C. for 4.5 minutes followed by 40 cycles of reactions, each of cycle being 95° C. for 30 seconds, 53° C. for 15 seconds and 72° C. for 30 seconds.

Using the PCR reaction liquid, PCR was carried out under the PCR conditions suitable for the kind of primer set.

The amplification product after PCR was incorporated into vectors included in a TA cloning kit (manufactured by Invitrogen Corporation under the trade name of TA cloning kit). *E. coli* (TOP 10) was transformed with the construct thus obtained. *E. coli* thus transformed was cultured at 37° C. overnight on LB agar medium (composition: 1% (w/v) tryptone, 0.5% (w/v) yeast extract, 1% (w/v) sodium chloride, and 1.5% (w/v) agar). Colonies of *E. coli* thus obtained were inoculated in LB liquid medium and cultured at 37° C. overnight. Then, a plasmid was purified from *E. coli* thus obtained using a plasmid extraction kit (manufactured by Sigma-Aldrich Corporation under the trade name of GenElute Plasmid Miniprep Kit). The amplification product that had been incorporated into the plasmids thus obtained was determined by BigDye terminator Cycle Sequencing, using a genetic analysis system (manufactured by Applied Biosystems Inc. under the trade name of ABI Prism 3100).

When cytosine in a CpG site is methylated (methylated CpG site), the CpG site appears as "CG" in the nucleotide sequence thus determined. On the other hand, when cytosine in a CpG site is unmethylated, (unmethylated CpG site), the CpG site appears as "TG" in the nucleotide sequence thus determined. Then, based on the nucleotide sequence of the amplification product thus determined, localization of a methylated CpG site and an unmethylated CpG site in HPV16 genomic DNA was analyzed. The results are shown in FIG. 2. FIG. 2 is a schematic diagram showing methylated CpG sites and unmethylated CpG sites in HPV16 genomic DNA integrated into a SiHa cell. In the figure, a closed circle represents methylated CpG sites and an open circle represents unmethylated CpG sites. Also, in the figure, numerical value in the column titled CpG site represents genome positions in GenBank NC_001526 (SEQ ID NO: 9).

From the results shown in FIG. 2, it is found that, among the nucleotide sequences of HPV16 integrated into genomic DNA of a SiHa cell (integrated HPV16), cytosine in each of a CpG site in L1 region and a CpG site in L2 region has been methylated. In contrast, it is found that cytosine in each of a CpG site in LCR and a CpG site in E6 region has been hardly methylated. Accordingly, from the results shown in FIG. 2, it is suggested that there is a possibility that integrated HPV16 causing onset of uterine cervical cancer can be detected by the presence or absence of HPV16 genomic DNA in which cytosine in CpG sites in L1 region and L2 region are methylated, whereas cytosine in CpG sites in LCR and E6 region are unmethylated.

Test Example 1

Among the uterine cervical tissues confirmed to be infected with HPV16, a normal tissue in which dysplasia had not pathologically developed and a cancer tissue were each thinly sliced into 20 µm-thick sections to prepare a normal tissue sample and a cancer tissue sample. To each of tissue samples thus obtained, 500 µL of a solution containing 1% (w/v) SDS and 0.1 M sodium hydroxide were added. Each of the mixtures thus obtained were incubated at 100° C. for 20 minutes. Subsequently, the mixtures after incubation were centrifuged at 4° C. to collect each of supernatants.

To each of the supernatants thus obtained, 500 µL of the bisulfite salt solution was added. Subsequently, the mixtures thus obtained were incubated at 80° C. for 40 minutes to carry out a bisulfite salt treatment. Nucleic acids contained in the solutions after the bisulfite salt treatment were purified by a nucleic acid purification kit (manufactured by QIAGEN under the trade name of QIAquick PCR purification kit). To the nucleic acids thus obtained, sodium hydroxide was added so as to have a final concentration of 0.3 M. Subsequently, the mixtures thus obtained were incubated at room temperature for 5 minutes. Thereafter, the products thus obtained were purified by a spin column for nucleic acid purification (manufactured by GE Healthcare under the trade name of MicroSpin S-300 HR Columns), whereby analytical samples were obtained.

To 4 µL of the analytical samples, 2 µL of reagent (trade name: ×10 buffer) contained in a PCR reagent (manufactured by Roche Diagnostics under the trade name of FastStart Taq DNA polymerase), 0.16 µL of DNA polymerase (trade name: FastStart Taq DNA polymerase (5 U/µL)), 1.6 µL of 2.5 mM dNTP mixture, 0.8 µL of an aqueous solution of forward primer (10 µM), 0.8 µL of an aqueous solution of reverse primer (10 µM), and 10.64 µL of water were added to prepare a PCR reaction liquid.

A primer set consisting of the forward primer and the reverse primer used and PCR thermal profiles are shown in Table 3.

TABLE 3

| | Primer | Nucleotide sequence | SEQ ID NO. | Thermal profile of PCR |
|---|---|---|---|---|
| Example 1 | 16L1/LCR-F | 5'-GAAGGTTAAATTAAAATTTATATTAGGAAAACGA-3' | 10 | (3) |
| | 16L1/LCR-R | 5'-AATTCAATTAAAACTACAAAATAACCACTAACACT-3' | 11 | |
| Comparative Example 1 | 16L1Me1-F | 5'-GTTGGTATTGTTGGTGAAAATGTATTAGAC-3' | 12 | (4) |
| | 16L1Me1-R | 5'-CCAACAAATACCATTATTATAACCCTATACTCG-3' | 13 | |
| Comparative Example 2 | 16LCRUnMe1-F | 5'-TGTATGTTTTTTGTTTGTTATGTG-3' | 14 | (5) |
| | 16LCRUnMe1-R | 5'-TACCTAACAACAATATATAAAACATTAACA-3' | 15 | |

In Table 3, the primer set of Example 1 consists of 16L1/LCR-F, which is the forward primer, and 16L1/LCR-R, which is the reverse primer. The 16L1/LCR-F hybridizes with a site corresponding to L1 region containing a given methylated CpG site in a nucleic acid that has been subjected to the bisulfite salt treatment, which corresponds to HPV16 genomic DNA. The 16L1/LCR-R hybridizes with a site corresponding to LCR containing a given unmethylated CpG site in a nucleic acid that has been subjected to the bisulfite salt treatment, which corresponds to HPV16 genomic DNA. That is, when a nucleic acid obtained by subjecting HPV16 genomic DNA in which cytosine in a CpG site in L1 region is methylated and cytosine in a CpG site in LCR is unmethylated to the bisulfite salt treatment is contained in an analytical sample, an amplification product will be generated by carrying out PCR using the primer set of Example 1.

In Table 3, the primer set of Comparative Example 1 consists of 16L1Me1-F, which is the forward primer, and 16L1Me1-R, which is the reverse primer. The 16L1Me1-F and 16L1Me1-R each hybridizes with sites corresponding to the L1 region containing a given methylated CpG site in a nucleic acid that has been subjected to the bisulfite salt treatment, which corresponds to HPV16 genomic DNA. That is, when a nucleic acid obtained by subjecting HPV16 genomic DNA in which cytosine in a CpG site in L1 region is methylated to the bisulfite salt treatment is contained in an analytical sample, an amplification product is generated by carrying out PCR using the primer set of Comparative Example 1.

In Table 3, the primer set of Comparative Example 2 consists of 16LCRUnMe1-F, which is the forward primer, and 16LCRUnMe1-R, which is the reverse primer. The aforementioned 16LCRUnMe1-F and 16LCRUnMe1-R each hybridizes with sites corresponding to the LCR containing a certain unmethylated CpG site in a nucleic acid that has been subjected to the bisulfite salt treatment, which corresponds to HPV16 genomic DNA. That is, when a nucleic acid obtained by subjecting HPV16 genomic DNA in which cytosine in a CpG site in LCR is unmethylated to the bisulfite salt treatment is contained in an analytical sample, an amplification product will be generated by carrying out PCR using the primer set of Comparative Example 2.

Also, in Table 3, PCR thermal profile (3) represents conditions for carrying out the reaction of incubation at 95° C. for 4.5 minutes followed by 45 cycles of reactions, each cycle being 95° C. for 30 seconds, 60° C. for 15 seconds and 72° C. for 30 seconds. PCR thermal profile (4) represents conditions for carrying out the reaction of incubation at 95° C. for 4.5 minutes followed by 45 cycles of reactions, each cycle being 95° C. for 30 seconds, 63° C. for 15 seconds and 72° C. for 30 seconds. PCR thermal profile (5) represents conditions for carrying out the reaction of incubation at 95° C. for 4.5 minutes followed by 45 cycles of reactions, each cycle being 95° C. for 30 seconds, 56° C. for 15 seconds, and 72° C. for 30 seconds.

Figure 3:
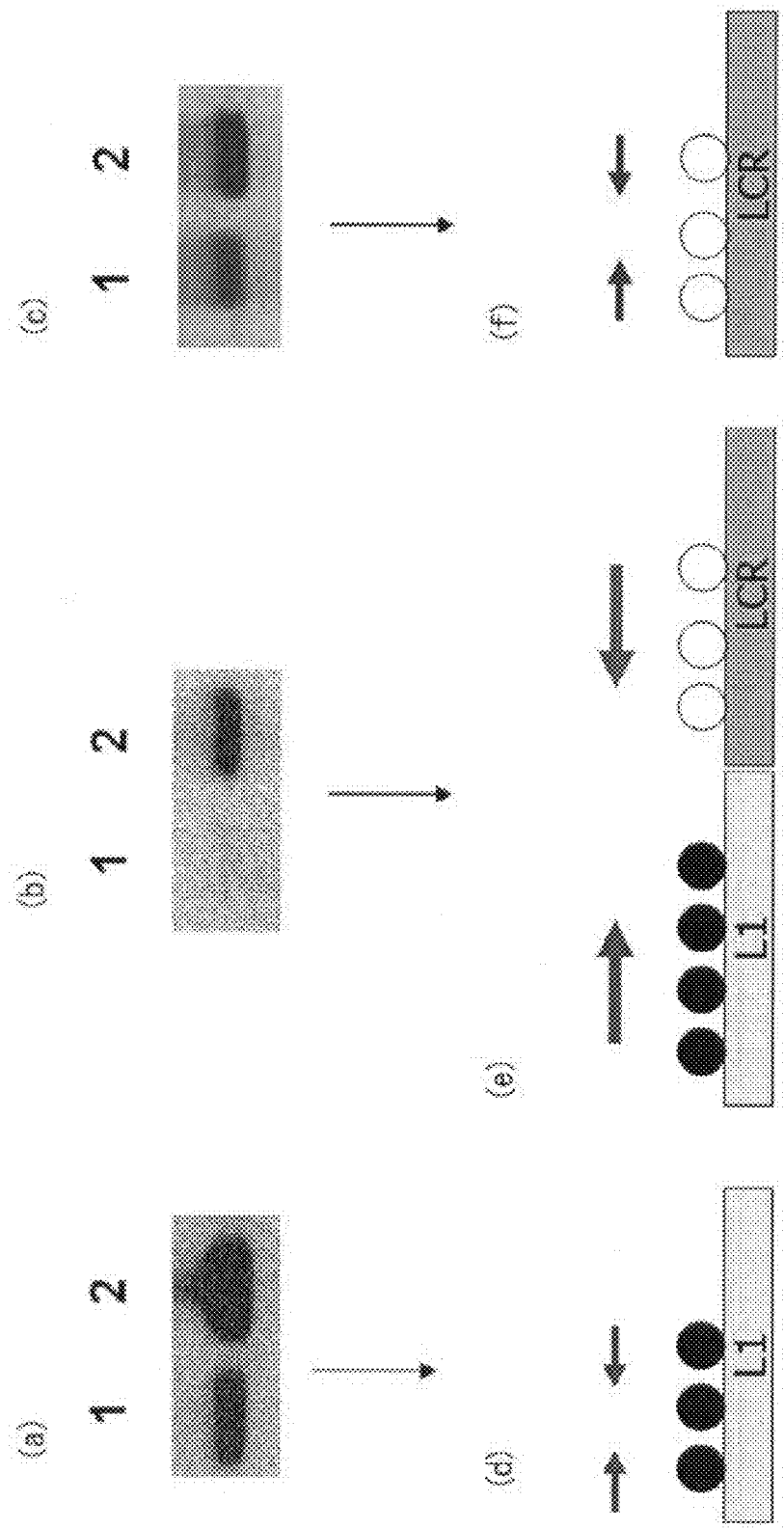
FIG. 3 is an electrophoretogram showing the resulting amplification products of nucleic acid amplification using each of the primer sets of Example 1 and Comparative Examples 1 and 2, and each of the analytical samples prepared from a normal tissue sample and a cancer tissue sample.

PCR was carried out using the PCR reaction liquid under PCR conditions suitable for the kind of primer set, thereby confirming the presence or absence of an amplification product. The results are shown in FIG. 3. FIG. 3 is an electrophoretogram showing the resulting amplification products of nucleic acid amplification using each of the primer sets of Example 1 and Comparative Examples 1 and 2, and each of the analytical samples prepared from a normal tissue sample and a cancer tissue sample. Lane 1 in panels (a) to (c) in FIG. 3 indicates the amplification product obtained by using a nucleic acid obtained from the normal tissue sample, and lane 2 indicates the amplification product obtained by using a nucleic acid obtained from the cancer tissue sample. Also, panel (a) in FIG. 3 shows the results obtained by using the primer set of Comparative Example 1, panel (b) shows the results obtained by using the primer set of Example 1, and panel (c) shows the results obtained by using the primer set of Comparative Example 2. Panels (d) to (f) schematically show a state of methylation or unmethylation in a gene region in HPV genomic DNA, which corresponds to the nucleic acid to be amplified. In panels (d) to (f), a closed circle and an open circle schematically show the presence of methylated cytosine and the presence of unmethylated cytosine, respectively.

As apparent from the results shown in panel (a) in FIG. 3, when the primer set of Comparative Example 1 has been used, an amplification product has been detected in lane 1 and lane 2. That is, an amplification product is obtained from both of the analytical sample prepared from the normal tissue and that prepared from the uterine cervical cancer tissue, with the primer set of Comparative Example 1. From this result, it is found that the normal tissue and the uterine cervical cancer tissue cannot be distinguished from each other only by detecting methylated L1 region (L1 region in which cytosine in a CpG site is methylated).

Further, as apparent from the results shown in panel (c) in FIG. 3, when the primer set of Comparative Example 2 has been used, an amplification product has been detected in lane 1 and lane 2. That is, an amplification product is obtained from both of the analytical sample prepared from the normal tissue and that prepared from the uterine cervical cancer tissue, with the primer set of Comparative Example 2. From this result, it is found that the normal tissue and the uterine cervical cancer tissue cannot be distinguished from each other only by detecting unmethylated LCR (LCR in which cytosine in a CpG site is unmethylated).

In contrast, as apparent from the results shown in panel (b) in FIG. 3, when the primer set of Example 1 has been used, no amplification product has been detected in lane 1, whereas an amplification product has been detected in lane 2. That is, it is found that no amplification product is obtained when the analytical sample prepared from the normal tissue is used, whereas an amplification product is obtained when the analytical sample prepared from the uterine cervical cancer tissue is used. As shown in panel (e) in FIG. 3, when the primer set of Example 1 is used, a nucleic acid corresponding to a continuous region from a site in a nucleic acid corresponding to methylated L1 region with which a primer hybridizes to a site in a nucleic acid corresponding to unmethylated LCR with which a primer hybridizes is targeted for amplification. Accordingly, the primer set of Example 1 enables amplification of only a nucleic acid that has been subjected to the bisulfite salt treatment, which corresponds to a continuous nucleic acid including certain L1 region and LCR in HPV16 genomic DNA contained in the HPV-infected cell 2 shown in the Table 1. As a result, by using the primer set of Example 1, it becomes possible to distinguish the normal tissue from the uterine cervical cancer tissue.

From the above results, it was suggested that a cancer cell caused by HPV can be detected by using the primer set consisting of the first primer which hybridizes with a nucleic acid consisting of a nucleotide sequence in which cytosine present in a site other than a CpG site is converted into another base in a nucleotide sequence having a CpG site in L1 region of HPV and the second primer which hybridizes with a nucleic acid consisting of a nucleotide sequence in which cytosine is converted into another base in a nucleotide sequence having a CpG site in LCR of HPV.

Experimental Example 2

By similar operations to Experimental Example 1, using C4-1 cell, which is an uterine cervical cancer-derived cell line having the HPV18 genome integrated into its chromosome, a methylated CpG site and an unmethylated CpG site in the HPV18 genome were analyzed. Specifically, except that genomic DNA of the C4-1 cell was used in place of genomic DNA of the SiHa cell and PCR reaction was carried out using the primer set and PCR thermal profile (6) shown in Table 4 in place of the primer set and PCR thermal profiles shown in. Table 2, similar operations to Experimental Example 1 were carried out to determine the nucleotide sequence of an amplification product.

TABLE 4

| Primer | Nucleotide Sequence | SEQ ID No. | Tm (° C.) | Thermal profile of PCR |
|---|---|---|---|---|
| Msp10F(18) | 5'-TAAAATATGTTTTGTGGTTTTGTG-3' | 17 | 59.25 | (6) |
| Msp10R(18) | 5'-ATAATTATACAAACCAAATATACAATT-3' | 18 | 54.36 | |
| Msp7F(18) | 5'-AGATTTAGATTAATATTTTTTTGGA-3' | 19 | 55.25 | (6) |
| Msp7R(18) | 5'-AAATTAAAATTTACAATAATACCAAC-3' | 20 | 54.8 | |
| 3F(18) | 5'-GTTATTTGATTTAAATAAATTTGGTTTATTTGA-3' | 21 | 62.74 | (6) |
| 3R(18) | 5'-CCAAAAATACCTAACAAAAAACTACTCA-3' | 22 | 62.17 | |
| Msp8F(18) | 5'-TGTTTAATATTTTGTTTATTTTTAATATG-3' | 23 | 56.22 | (6) |
| Msp8R(18) | 5'-TATCTTACAATAAAATATTCAATTCC-3' | 24 | 55.49 | |

In Table 4, PCR thermal profile (6) represents conditions for carrying out 40 cycles of reactions after keeping the sample at 95° C. for 4.5 minutes, where one cycle consists of 95° C. for 30 seconds, 54° C. for 30 seconds, and 72° C. for 40 seconds.

Figure 4:
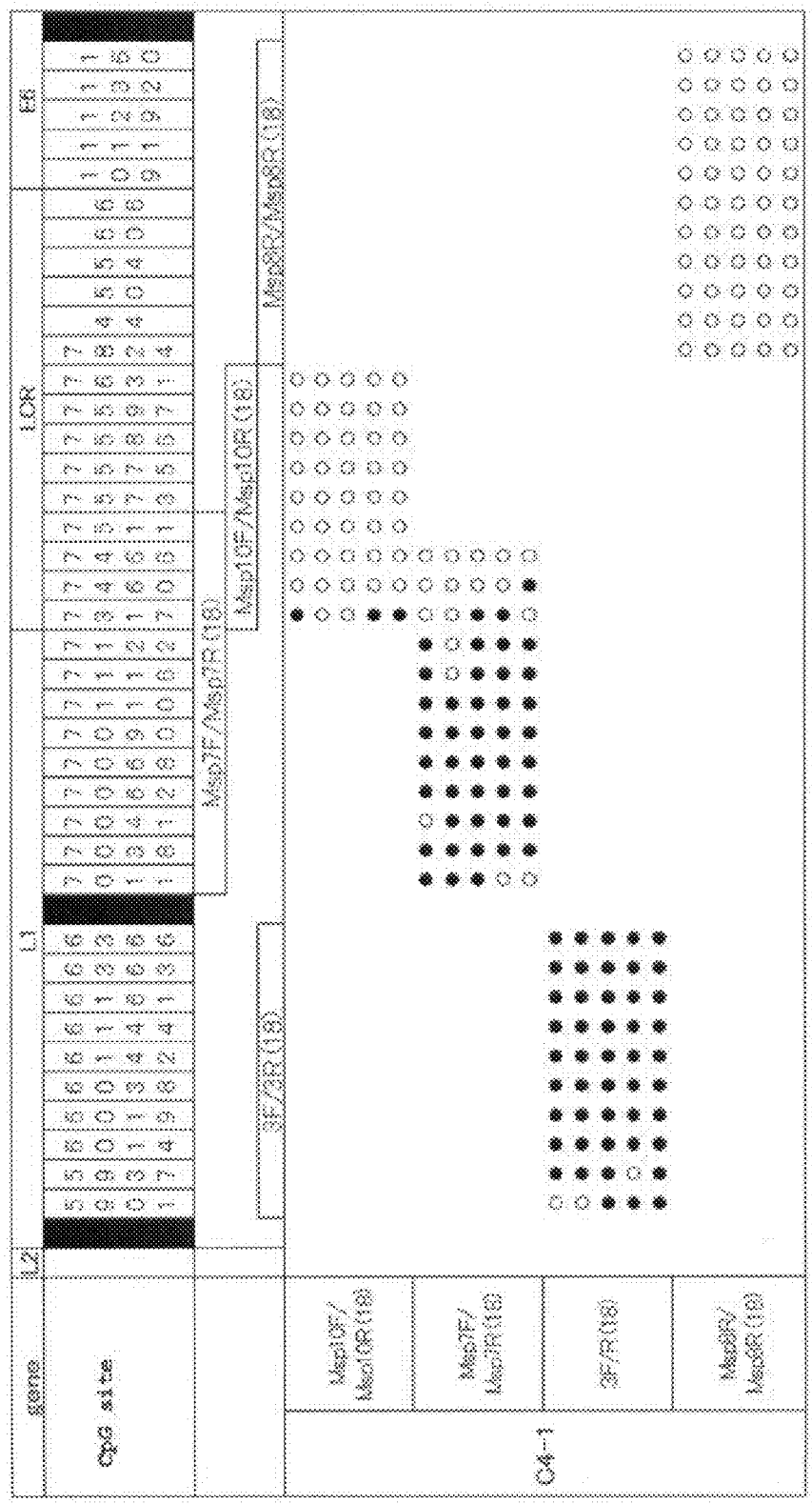
FIG. 4 is a schematic diagram showing methylated CpG sites and unmethylated CpG sites in HPV18 genomic DNA integrated into a C4-1 cell.

Then, based on the nucleotide sequence of the amplification product thus determined, localization of a methylated CpG site and an unmethylated CpG site in HPV18 genomic DNA was analyzed. The results are shown in FIG. 4. FIG. 4 is a schematic diagram showing methylated CpG sites and unmethylated CpG sites in HPV18 genomic DNA integrated into C4-1 cell. In the figure, a closed circle represents a methylated CpG site and an open circle represents a unmethylated CpG site. Also, in the figure, numerical values in the column titled "CpG site" represent genome positions in GenBank NC_001357 (SEQ ID NO: 16).

From the results shown in FIG. 4, it is found that, similarly to HPV16 integrated into genomic DNA of SiHa cell (integrated HPV16), cytosine in a CpG site in L1 region is methylated whereas cytosine in each of CpG sites in LCR and E6 region is unmethylated, also in HPV18 integrated into genomic DNA of C4-1 cell (integrated HPV18). From the above results, it is suggested that there is a possibility that by using the primer set of the present invention integrated HPV causing onset of uterine cervical cancer can be detected irrespective of the kind of HPV.

Test Example 3

Fourteen kinds of uterine cervical tissues each of which was surgically resected from a subject and confirmed to have been infected with HPV16 were provided as paraffin blocks (hereinafter, referred to as "surgically-resected sample"). Also, seven kinds of uterine cervical tissues each of which was collected by scratching the uterine cervix of a subject under colposcopic observation and confirmed to have been infected with HPV16 were provided as paraffin blocks (hereinafter, referred to as "biopsy sample"). Each of the paraffin block was thinly sliced into 10 μm-thick sections to give tissue samples.

The surgically-resected sample and the biopsy sample both include tissues that have been diagnosed to be at a stage of dysplasia or a more severe stage by conventional tissue diagnosis. Among the fourteen kinds of surgically-resected samples, one of them is a sample of mild-grade dysplasia (CIN1), four kinds are samples of moderate-grade dysplasia (CIN2), four kinds are samples of high-grade dysplasia (CIN3), four kinds are samples of cancer (SCC), and another one is a normal sample. Also, among the biopsy samples, two of them are samples of mild-grade dysplasia (CIN1), another two are samples of high-grade dysplasia (CIN3), and the other three are samples of cancer (SCC).

To a 1.5 mL tube, three sections of a tissue sample obtained from the same paraffin block and 1 mL of xylene were added. The mixture thus obtained was centrifuged at 12000 rpm for 10 minutes. After centrifugation, the resulting supernatant was removed and 1 mL of 100% by volume of ethanol was added to the resulting pellet to make a suspension. The suspension thus obtained was centrifuged at 12000 rpm for 10 minutes. After centrifugation, the resulting supernatant was removed, and 100% by volume of ethanol was added to the resulting pellet again to make a suspension. The suspension thus obtained was centrifuged again at 12000 rpm for 10 minutes. After centrifugation, the resulting supernatant was removed and the resulting pellet was dried. The pellet thus obtained will be hereinafter referred to as "dried pellet".

To the dried pellet obtained from the surgically-resected sample, 700 μL of a solution containing 1% (w/v) SDS and 0.1 M sodium hydroxide was added. Also, to the dried pellet obtained from the biopsy sample, 500 μL of a solution containing 1% (w/v) SDS and 0.1 M sodium hydroxide was added. Each of the mixtures thus obtained was incubated at 100° C. for 20 minutes. After incubation, each of the mixtures was centrifuged at a temperature of 4° C. and at 12000 rpm for 10 minutes to collect the supernatant.

To the supernatant obtained from the surgically-resected sample, 700 μL of the bisulfite salt solution was added and mixed. Also, to the supernatant obtained from the biopsy sample, 500 μL of the bisulfite salt solution was added and mixed. Subsequently, each of the mixtures thus obtained was incubated at 80° C. for 40 minutes to carry out a bisulfite salt treatment. A nucleic acid contained in a solution after the bisulfite salt treatment was purified by a nucleic acid purification kit (manufactured by QIAGEN under the trade name of QIAquick PCR Purification Kit). To the nucleic acid thus obtained, sodium hydroxide was added so as to have a final concentration of 0.3 M. Subsequently, the mixture thus obtained was incubated at room temperature for 5 minutes. Thereafter, the product thus obtained was purified by a spin column for nucleic acid purification (manufactured by GE Healthcare under the trade name of MicroSpin S-300 HR Columns), whereby analytical samples were obtained.

A PCR reaction liquid was prepared by performing operations similar to those in Test Example 1, except that the analytical sample derived from the surgically-resected sample was used as an analytical sample. Also, a PCR reaction liquid was prepared by carrying out the same operations as those in Test Example 1, except that the analytical sample derived from the biopsy sample was used as an analytical sample and that the amount of the analytical sample was adjusted to 2 μL. As a primer set for the PCR reaction liquid, a primer set of Example 1 consisting of a primer consisting of the nucleotide sequence shown in SEQ ID NO: 10 and a primer consisting of the nucleotide sequence shown in SEQ ID NO: 11 was used.

The PCR conditions when the PCR reaction liquid containing the analytical sample derived from the surgically-resected sample is used are the same as those of PCR thermal profile (3) in Table 3. The PCR conditions when the PCR reaction liquid containing the analytical sample derived from the biopsy sample is used are conditions for carrying out the reaction of incubation at 95° C. for 4.5 minutes followed by 40 cycles of reactions, each cycle being 95° C. for 30 seconds, 60° C. for 15 seconds and 72° C. for 30 seconds.

Figure 5:
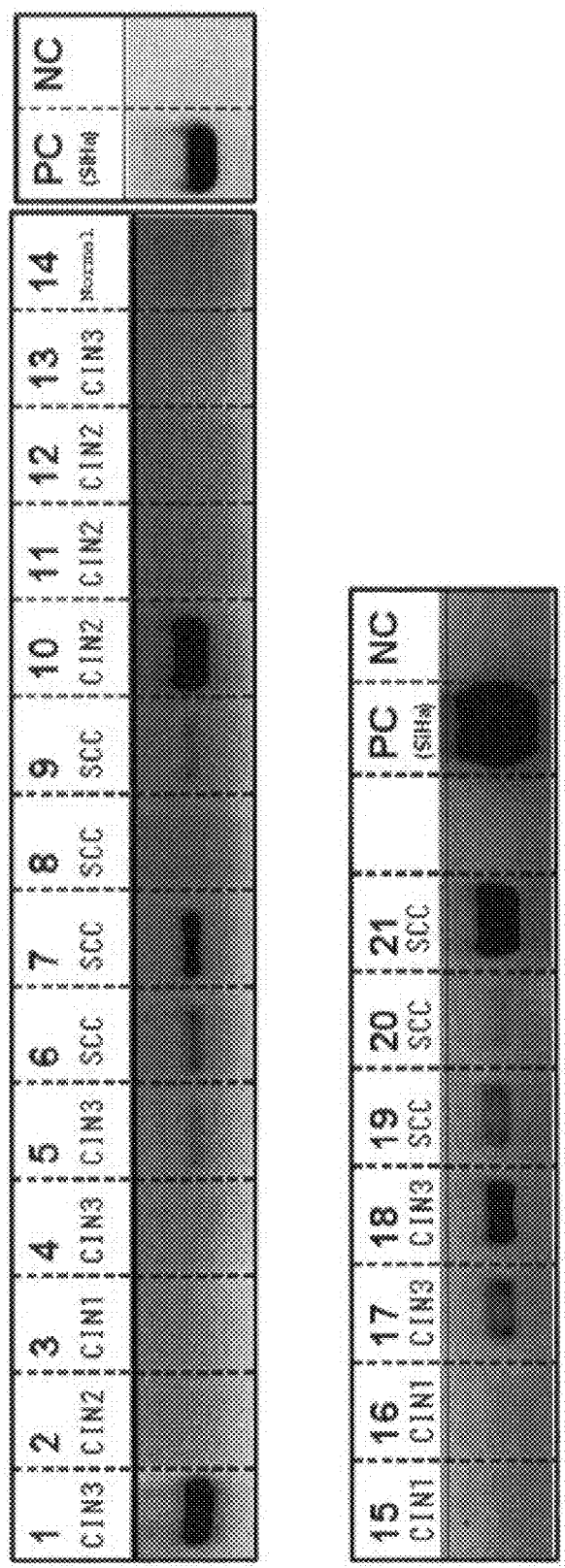
FIG. 5 is an electrophoretogram showing the resulting amplification product of nucleic acid amplification using the primer set of Example 1 and each of the analytical samples prepared from a surgically-resected sample and a biopsy sample.

PCR was carried out using the PCR reaction liquid under PCR conditions suitable for the kind of primer set, and the presence or absence of an amplification product was confirmed. The results are shown in FIG. 5. FIG. 5 is an electrophoretogram showing the resulting amplification products of nucleic acid amplification using the primer set of Example 1 and each of the analytical samples prepared from the surgically-resected sample and the biopsy sample. In FIG. 5, lane 1 shows the result obtained by using the surgically-resected sample of CIN3, lane 2 shows the result obtained by using the surgically-resected sample of CIN2, lane 3 shows the result obtained by using the surgically-resected sample of CIN1, lane 4 shows the result obtained by using the surgically-resected sample of CIN3, lane 5 shows the result obtained by using the surgically-resected sample of CIN3, lane 6 shows the result obtained by using the surgically-resected sample of SCC, lane 7 shows the result obtained by using the surgically-resected sample of SCC, lane 8 shows the result obtained by using the surgically-resected sample of SCC, lane 9 shows the result obtained by using the surgically-resected sample of SCC, lane 10 shows the result obtained by using the surgically-resected sample of CIN2, lane 11 shows the result obtained by using the surgically-resected sample of CIN2, lane 12 shows the result obtained by using the surgically-resected sample of CIN2, lane 13 shows the result obtained by using the surgically-resected sample of CIN3, and lane 14 shows the result obtained by using the surgically-resected sample of a normal tissue, lane 15 shows the result obtained by using the biopsy sample of CIN1, lane 16 shows the result obtained by using the biopsy sample of CIN1, lane 17 shows the result obtained by using the biopsy sample of CIN3, lane 18 shows the result obtained by using the biopsy sample of CIN3, lane 19 shows the result obtained by using the biopsy sample of SCC, lane 20 shows the result obtained by using the biopsy sample of SCC, and lane 21 shows the result obtained by using the biopsy sample of SCC. In FIG. 5, PC shows the result obtained by using a nucleic acid obtained by subjecting genomic DNA of SiHa cell to a bisulfite salt treatment as an analytical sample, and NC shows the result obtained by using distilled water as an analytical sample. Further, the results of analyzing the results shown in FIG. 5 based on the stage of dysplasia are shown in Table 5. In Table 5, "L1-LCR positive" indicates a sample from which an amplification product was detected. Also in Table 5, a rate (%) of the number of L1-LCR positive samples with respect to the total number of samples is indicated in parentheses.

TABLE 5

|  | L1-LCR positive (%) | Total number of samples |
|---|---|---|
| Normal | 0(0%) | 1 |
| CIN1 | 0(0%) | 3 |
| CIN2 | 1(25%) | 4 |
| CIN3 | 4(67%) | 6 |
| SSC | 6(86%) | 7 |
| Total |  | 21 |

From the results shown in FIG. 5 and Table 5, it is found that, with the primer set of Example 1, when an analytical sample prepared from a tissue determined to be at a stage of high-grade dysplasia (CIN3) or a more severe stage by tissue diagnosis is used, an amplification product is obtained at a high rate, whereas when an analytical sample prepared from a tissue determined to be at a stage of moderate-grade dysplasia (CIN2) or a milder stage by tissue diagnosis is used, an amplification product is obtained at a low rate. From the above results, it is found that by the primer set of Example 1, whether or not a tissue obtained as a clinical specimen such as a surgically-resected sample and a biopsy sample is at a stage of high-grade dysplasia or a more severe stage can be determined.

Test Example 4

Using a paraffin block of cancer tissue that was surgically resected from a subject and confirmed to have been infected with HPV18, and a paraffin block of uterine cervical tissue that was surgically resected from a subject and confirmed to have been infected with HPV58 and diagnosed as a tissue at a stage of CIN3 (surgically-resected sample) and a paraffin block of uterine cervical tissue derived from a patient that was collected by scratching the uterine cervix of a subject under colposcopic observation and confirmed to have been infected with HPV58 and in addition diagnosed to be at a stage of CIN3 (biopsy sample), an analytical sample of each of them was obtained by performing operations similar to those in Test Example 2.

To 2 μL of the analytical sample, 1.5 μL of reagent (×10 buffer) contained in a PCR reagent (manufactured by TAKARA BIO INC. under the trade name of TaKaRa EX Taq (trademark) Hot Start Version), 0.075 μL of DNA polymerase (trade name: TaKaRa Ex Taq HS (5 U/μL)), 1.2 μL of 2.5 mM dNTP mixture, 0.6 μL of an aqueous solution of forward primer (10 mM), 0.6 μL of an aqueous solution of reverse primer (10 mM), and 9.025 μL of water were added to prepare a PCR reaction liquid.

Primer sets each consisting of the forward primer and the reverse primer used for the analytical sample derived from the sample containing HPV18 are shown in Table 6. Primer sets each consisting of the forward primer and the reverse primer used for the analytical sample derived from the sample containing HPV58 are shown in Table 7.

TABLE 6

| Primer | Nucleotide sequence | SEQ ID No. | Tm (° C.) | Thermal profile of PCR |
|---|---|---|---|---|
| Msp10F(18) | 5'-TAAAATATGTTTTGTGGTTTTGTG-3' | 17 | 59.25 | (6) |
| Msp10R(18) | 5'-ATAATTATACAAACCAAATATACAATT-3' | 18 | 54.36 | |
| Msp7F(18) | 5'-AGATTTAGATTAATATTTTTTGGA-3' | 19 | 55.25 | (6) |
| Msp7R-2(18) | 5'-ATATATAACCCAACAAACAACAC-3' | 25 | 56.03 | |
| 3F(18) | 5'-GTTATTTGATTTAAATAAATTTGGTTTATTTGA-3' | 21 | 62.74 | (6) |
| 3R-2(18) | 5'-TCCATAACACCATATCCAATATCTACC-3' | 26 | 63.38 | |

TABLE 7

| Primer | Nucleotide sequence | SEQ ID No. | Tm (° C.) | Thermal profile of PCR |
|---|---|---|---|---|
| 5F(58) | 5'-TGGTTAGTGAATTTTATGGGG-3' | 27 | 60.07 | (6) |
| 5R-2(58) | 5'-TTACAAAACTAAAAAACAAACTATAAATCA-3' | 28 | 59.4 | |
| 2F(58) | 5'-ATGGTGTTGATTTTATGTTGTATT-3' | 29 | 57.8 | (6) |
| 2R(58) | 5'-AACTATCCCCTACCTATTTCAAAAC-3' | 30 | 60.35 | |
| 3F(58) | 5'-TTAATATTTTGGAGGATTGGTAAT-3' | 31 | 58.32 | (6) |
| 3R(58) | 5'-ATATAATAAAATAATATAAATACCACAACA-3' | 32 | 55.07 | |
| 4F(58) | 5'-AATTAGGTTTTAAAGTAAAGTTTAGATTA-3' | 33 | 55.94 | (6) |
| 4R(58) | 5'-TTATTTAAATTATAATTTAAAAAAAACAC-3' | 34 | 55.11 | |
| 1F(58) | 5'-TTTTATTTTTATTTTGTGTATGTAAT-3' | 35 | 54.07 | (6) |
| 1R-2(58) | 5'-TAATCCTACAATAACCTACCAAAAA-3' | 36 | 58.53 | |

Figure 7:
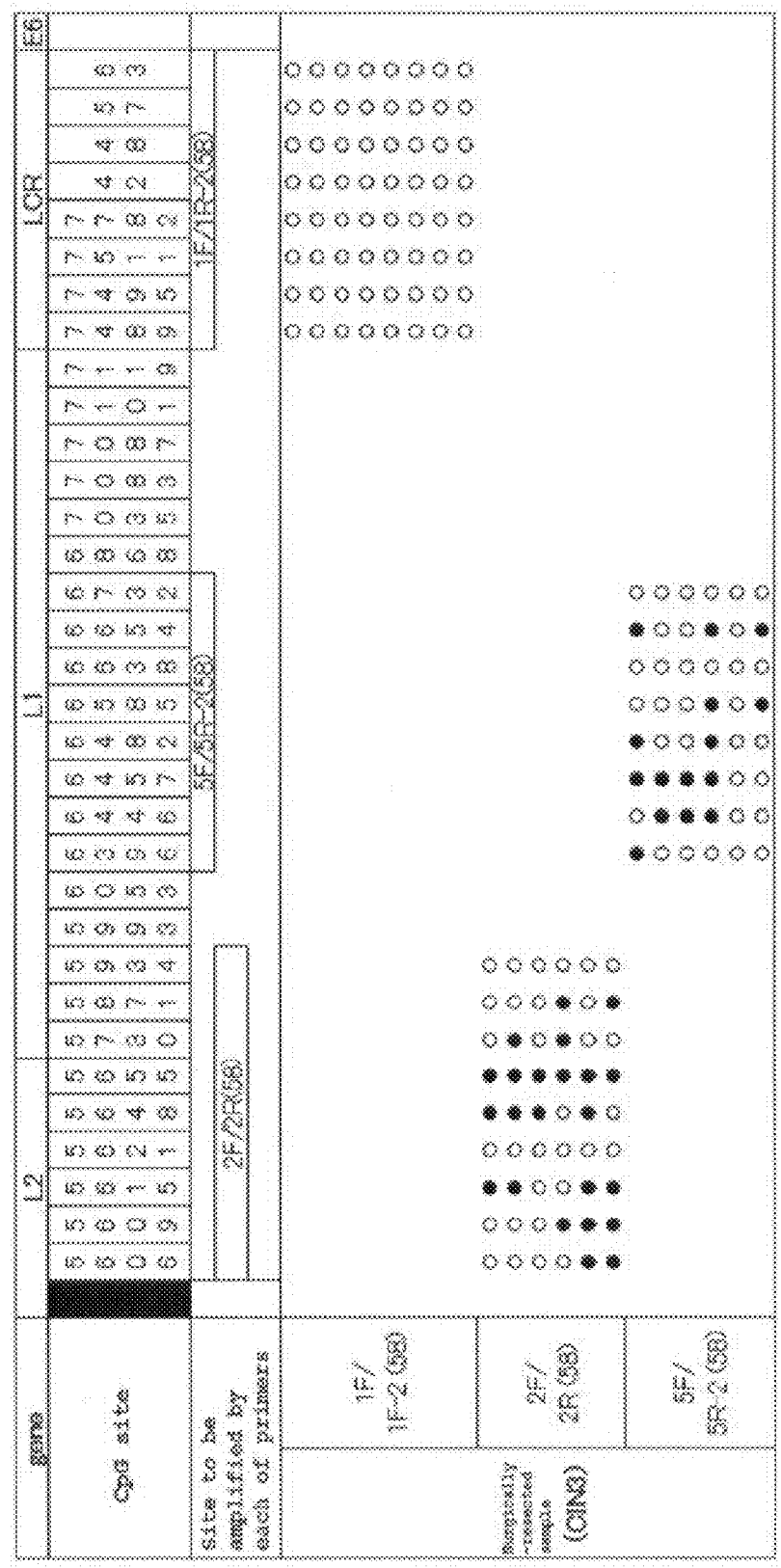
FIG. 7 is a schematic diagram showing methylated CpG sites and unmethylated CpG sites in HPV58 genomic DNA derived from a surgically-resected sample.
Figure 8:
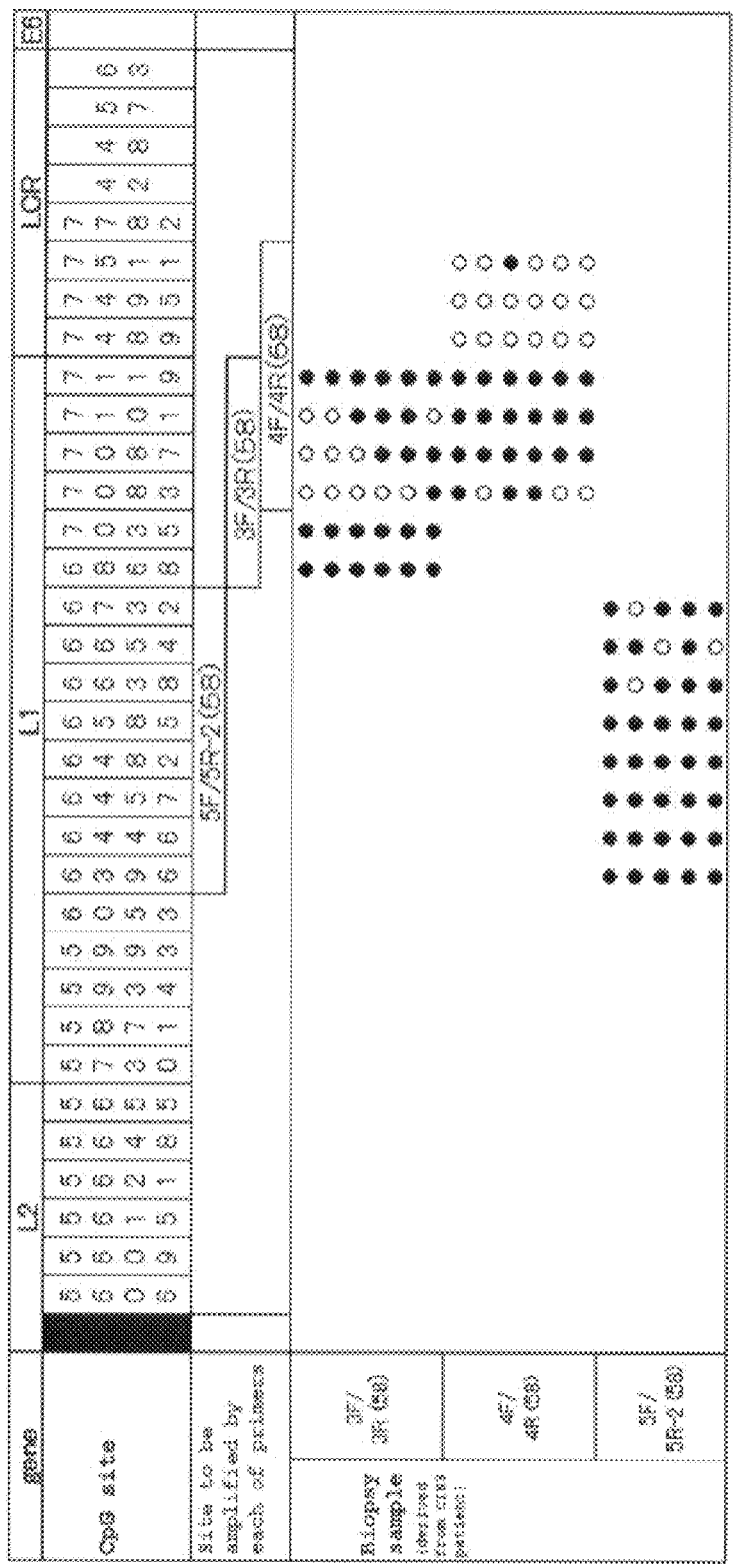
FIG. 8 is a schematic diagram showing methylated CpG sites and unmethylated CpG sites in HPV58 genomic DNA derived from a biopsy sample.

Using the PCR thermal profile (6) used in Experimental Example 2 and each of the analytical samples derived from the surgically-resected sample and the biopsy sample as the PCR conditions, methylated CpG sites and unmethylated CpG sites in genomic DNA of each of HPV18 and HPV58 were analyzed by performing operations similar to those of Experimental Example 1. The results are shown in FIGS. 6 to 8.

Figure 6:
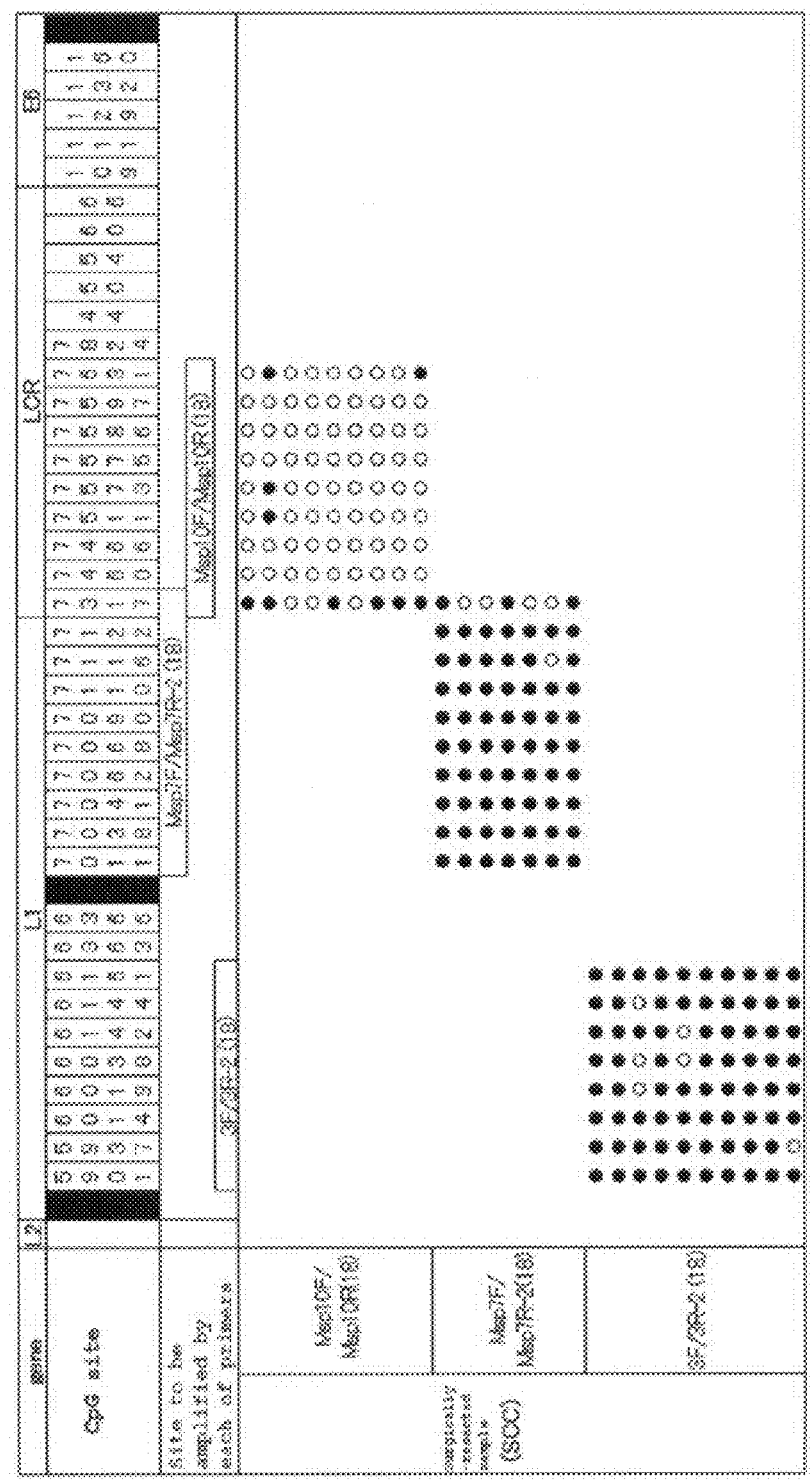
FIG. 6 is a schematic diagram showing methylated CpG sites and unmethylated CpG sites in HPV18 genomic DNA derived from a surgically-resected sample.

FIG. 6 is a schematic diagram showing methylated CpG sites and unmethylated CpG sites in HPV18 genomic DNA derived from the surgically-resected sample. FIG. 7 is a schematic diagram showing methylated CpG sites and unmethylated CpG sites in HPV58 genomic DNA derived from the surgically-resected sample. FIG. 8 is a schematic diagram showing methylated CpG sites and unmethylated CpG sites in HPV58 genomic DNA derived from the biopsy sample. In the figure, a closed circle represents a methylated CpG site and an open circle represents an unmethylated CpG site. Also, in FIG. 6, numerical values in the column titled "CpG site" represent genome positions in GenBank NC_001357 (SEQ ID NO: 16). Also, in FIGS. 7 and 8, numerical values in the column titled "CpG site" represent genome positions in GenBank NC_001443 (SEQ ID NO: 37).

From the results shown in FIG. 6, it is found that, in HPV18 derived from the cancer tissue confirmed to have been infected with HPV18, cytosine in a CpG site in L1 region is frequently methylated, cytosine in a CpG site in LCR is hardly methylated, and cytosine in a CpG site in E6 region is unmethylated. Also, from the results shown in FIG. 7, it is found that, in HPV58 derived from the uterine cervical tissue that was confirmed to have been infected with HPV58 and diagnosed as CIN3, cytosine in CpG sites in L1 region and L2 region is frequently methylated, and cytosine in a CpG site in LCR is unmethylated. Further, from the results shown in FIG. 8, it is found that, in HPV58 derived from the uterine cervical tissue obtained from a patient under colposcopic observation and confirmed to have been infected with HPV58 and diagnosed as CIN3, cytosine in a CpG site in L1 region is frequently methylated, and cytosine in a CpG site in LCR is hardly methylated.

From the results, it is suggested that, regardless of the kinds of HPV, HPV causing onset of uterine cervical cancer can be detected by using the primer set consisting of the first primer which hybridizes with a nucleic acid consisting of a nucleotide sequence in which cytosine present in a site other than a CpG site is converted into another base in a nucleotide sequence having a CpG site in L1 region or L2 region of HPV, and the second primer which hybridizes with a nucleic acid consisting of a nucleotide sequence in which cytosine is converted into another base in a nucleotide sequence having a CpG site in LCR or E6 region of HPV. Also, it was suggested that, according to the primer set, whether or not a tissue obtained as a clinical specimen such as a surgically-resected sample and a biopsy sample is at a stage of high-grade dysplasia or a more severe stage can be determined.

Preparation Example 1

A diagnostic kit for cancer caused by HPV or a diagnostic kit for a stage of dysplasia was prepared. One example thereof is shown below. The kit includes a nuclease-free container containing an aqueous solution of each primer of the below-described primer sets and a nuclease-free container containing a bisulfite salt solution (10M aqueous solution of sodium bisulfite), which is an unmethylated cytosine-conversion agent.

The content of the diagnostic kit for cancer caused by HPV or the diagnostic kit for a stage of dysplasia:

Container 1
An aqueous solution of forward primer (an aqueous solution obtained by dissolving primer 16L1/LCR-F consisting of the nucleotide sequence shown in SEQ ID NO: 10 in nuclease-free water)
Container 2
An aqueous solution of reverse primer (an aqueous solution obtained by dissolving the primer 16L1/LCR-F consisting of the nucleotide sequence shown in SEQ ID NO: 10 in nuclease-free water)
Container 3
10M aqueous solution of sodium bisulfite Cancer caused by HPV can be diagnosed easily with high accuracy by performing operations similar to those of Test Example 1 using the above kit. Also, the stage of dysplasia can be diagnosed easily with high accuracy by performing operations similar to those of Test Example 3 using the above kit.

Sequence Listing Free Text
SEQ ID No.: 1 is a sequence of a primer.
SEQ ID No.: 2 is a sequence of a primer.
SEQ ID No.: 3 is a sequence of a primer.
SEQ ID No.: 4 is a sequence of a primer.
SEQ ID No.: 5 is a sequence of a primer.
SEQ ID No.: 6 is a sequence of a primer.
SEQ ID No.: 7 is a sequence of a primer.
SEQ ID No.: 8 is a sequence of a primer.
SEQ ID No.: 10 is a sequence of a primer.
SEQ ID No.: 11 is a sequence of a primer.
SEQ ID No.: 12 is a sequence of a primer.
SEQ ID No.: 13 is a sequence of a primer.
SEQ ID No.: 14 is a sequence of a primer.
SEQ ID No.: 15 is a sequence of a primer.
SEQ ID No.: 17 is a sequence of a primer.
SEQ ID No.: 18 is a sequence of a primer.
SEQ ID No.: 19 is a sequence of a-primer.
SEQ ID No.: 20 is a sequence of a primer.
SEQ ID No.: 21 is a sequence of a primer.
SEQ ID No.: 22 is a sequence of a primer.
SEQ ID No.: 23 is a sequence of a primer.
SEQ ID No.: 24 is a sequence of a primer.
SEQ ID No.: 25 is a sequence of a primer.
SEQ ID No.: 26 is a sequence of a primer.
SEQ ID No.: 27 is a sequence of a primer.
SEQ ID No.: 28 is a sequence of a primer.
SEQ ID No.: 29 is a sequence of a primer.
SEQ ID No.: 30 is a sequence of a primer.
SEQ ID No.: 31 is a sequence of a primer.
SEQ ID No.: 32 is a sequence of a primer.
SEQ ID No.: 33 is a sequence of a primer.
SEQ ID No.: 34 is a sequence of a primer.
SEQ ID No.: 35 is a sequence of a primer.
SEQ ID No.: 36 is a sequence of a primer.

The invention claimed is:

1. A method for detecting a cancer cell caused by HPV, comprising the steps of:
   (A) preparing a sample containing DNA from a cell of a subject;
   (B) converting unmethylated cytosine in DNA contained in the sample obtained in the step (A) into another base, to give a conversion sample such that in a nucleic acid in the L1 region or L2 region of HPV, cytosine present in a CpG site is not converted into another base, and in a nucleic acid sequence in the LCR or E6 region of HPV, a cytosine in a CpG site is converted into another base;
   (C) carrying out nucleic acid amplification reaction, by using the conversion sample obtained in the step (B), a first primer which hybridizes with said nucleic acid in the L1 region or L2 region of HPV, and a second primer which hybridizes with said nucleic acid in the LCR or E6 region of HPV, wherein the nucleic acid amplification reaction is to amplify a nucleic acid consisting of a continuous nucleotide sequence ranged from the site with which the first primer is hybridized to the site with which the second primer is hybridized; and
   (D) detecting a cancer cell caused by HPV based on the result of the nucleic acid amplification reaction of the step (C).

2. The method according to claim 1, wherein the step (A) comprises the steps of:
   (a) mixing a solution containing a surfactant with a cell of a subject, to give a mixture;
   (b) subjecting the mixture obtained in the step (a) to centrifugation, thereby precipitating an insoluble matter, to give a supernatant; and
   (c) collecting the supernatant obtained in the step (b).

3. The method according to claim 2, wherein the step (A) further comprises the step of:

(a1) subjecting the mixture obtained in the step (a) to a physical treatment, thereby liberating DNA from the cell, between the step (a) and the step (b), wherein, in the step (b), a product obtained in the step (a1) is subjected to centrifugation, thereby precipitating an insoluble matter, to give a supernatant.

4. The method according to claim 1, wherein the cell is from a uterine cervical tissue.

5. The method according to claim 1, wherein the first primer hybridizes with a nucleic acid consisting of a nucleotide sequence in which cytosine is present in a site other than a CpG in the L1 region of HPV.

6. The method according to claim 1, wherein the second primer hybridizes with a nucleic acid consisting of a nucleotide sequence in which cytosine is converted into another base in a nucleotide sequence having a CpG site in the LCR of HPV.

7. The method according to claim 1, wherein the another base is uracil.

8. The method according to claim 1, wherein the amplification reaction is a polymerase chain reaction, a strand displacement amplification, a ligase chain reaction, or a transcriptional amplification.

* * * * *